United States Patent [19]
VanBeek et al.

[11] Patent Number: 6,072,067
[45] Date of Patent: Jun. 6, 2000

[54] CYCLOPENTADIENE COMPOUND SUBSTITUTED WITH A HETERO ATOM-CONTAINING GROUP

[75] Inventors: Johannes A. M. VanBeek; Gerardus J. M. Gruter, both of Maastricht, Netherlands

[73] Assignee: DSM N.V., Geleen, Netherlands

[21] Appl. No.: 08/850,274

[22] Filed: May 2, 1997

[30] Foreign Application Priority Data

May 3, 1996 [NL] Netherlands ............................ 1003008

[51] Int. Cl.$^7$ ................................. C07F 17/00; C07F 7/00
[52] U.S. Cl. ................................. 556/11; 556/43; 556/53; 556/46; 556/58; 556/136; 556/140; 534/15; 526/127; 526/160; 526/943; 502/103; 502/117
[58] Field of Search .................................. 556/11, 43, 53, 556/46, 58, 136, 140; 502/103, 117; 526/127, 160, 943; 534/15

[56] References Cited

U.S. PATENT DOCUMENTS 5,563,284  10/1996  Frey et al. ................................. 556/53

FOREIGN PATENT DOCUMENTS

| 0 416 815 A2 | 3/1991 | European Pat. Off. . |
| 0 728 769 A1 | 8/1996 | European Pat. Off. . |
| 0 728 770 A1 | 8/1996 | European Pat. Off. . |
| 43 03 647 A1 | 8/1994 | Germany . |
| WO 96/13529 | 5/1996 | WIPO . |

OTHER PUBLICATIONS du Plooy et al., Organometallics, vol. 14, No. 7, pp. 3129–3131, Jul. 1995.

Szymoniak et al., "New Heterodifunctional Ligands for Organotransiton–Metal Chemistry: . . .", Journal of Organic Chemistry, 1990, vol. 55, pp. 1429–1432.

Ying Mu et al., "Use of Alkane Elimination in the One–step Synthesis of Organoscandium Complexes Containing a New Multidentate Cyclopentadienyl Ligand", *Organometallics*, 1996, vol. 15, pp. 2720–2726.

Chemical Abstracts, vol. 123, No. 13 (Sep. 1995), Abstract No. 169881.

Weinheim DE, K Hafner et al., "Synthesen und Reaktionen von Fulvenaldehyden", Chemische Berichte, 1963, vol. 661, pp. 52–75.

G. Kresze et al., "Substitierte Cyclopentadiene und ihre Diels–Alder–Reaktionen", Chemische Berichte, 1963, vol. 666, pp. 45–53.

Krut'ko, D.P. et al., "Tetramethyl(2–methylthioethyl)cyclopentadienly Complexes of Zirconium(IV): Synthesis, . . . Solutions", Russian Chemical Bulletin, 1996, vol. 45, No. 4.

Ulrich Siemeling, "$C_5Me_4(CH_2)_3OMe$: A Tentacle–bearing Cyclopentadienyl Ligand and Its Use in Complex Chemistry", J. Chem. Soc. Commun., 1992, vol. 18, pp. 1335–1336.

*Primary Examiner*—Porfirio Nazario-Gonzalez
*Attorney, Agent, or Firm*—Pillsbury Madison & Sutro LLP

[57] ABSTRACT

Polysubstituted cyclopentadiene-containing compound, in which at least one substituent is has the formula —$RDR'_n$, in which R is a linking group between the cyclopentadiene and the $DR'_n$ group, D is a hetero atom selected from group 15 or 16 of the Periodic Table of Elements or an aryl group, in which case R has at least the length of an ethylene group, R' is a hydrocarbon radical containing 1–20 carbon atoms (e.g., alkyl, aryl, aralkyl,. and the like, including straight chain, branched, cyclic, and derivatives thereof, and n is the number of R' groups bound to D (note that the R' groups may be identical or different).

12 Claims, No Drawings

CYCLOPENTADIENE COMPOUND SUBSTITUTED WITH A HETERO ATOM-CONTAINING GROUP

BACKGROUND OF THE INVENTION

1. Field of the Invention

The invention relates to a polysubstituted cyclopentadiene compound, of which at least one substituent is of the formula —RDR'$_n$, where R is a linking group between the cyclopentadiene and the group DR'$_n$, D is a hetero atom selected from group 15 or 16 of the Periodic Table of Elements, R' is a hydrocarbon radical containing 1–20 carbon atoms (e.g., alkyl, aryl, aralkyl, and the like, including straight chain, branched, cyclic, and derivatives thereof), and n is the number of R' groups bound to D.

2. Description of the Related Art

As referred to herein, cyclopentadiene will be abbreviated as Cp. The same abbreviation will be used for a cyclopentadienyl group if it is clear, from the context, whether cyclopentadiene itself or its anion is meant.

An overview of the influence of cyclopentadiene substituents on the catalytic activity of a metal complex comprising the substituted cyclopentadiene as a ligand was provided in *J. of Organomet. Chem.* 1994, 479, 1–29. It was observed that the chemical and physical properties of the metal complexes can be varied by modifying the substituents on the cyclopentadiene ring. However, no predictions were made concerning the effect of the specific substituents of the invention. It was emphasized that "[a]n important feature of these catalyst systems is that tetravalent Ti centres are required for catalytic activity" (note that Ti was given as an example of a metal in the cyclopentadienyl-substituted metal complex).

Szymoniak et al., *J. Org. Chem.* 1990, 55, 1429–1432, disclosed a tetramethyl-substituted cyclopentadiene containing a diphenylphosphinyl group as a fifth substituent, which is coupled to the Cp either directly or via an ethylene group. The synthesis method described is highly specific, and there is no teaching whether or how, Cp compounds substituted in other ways can be obtained.

Jutzi et al., *Synthesis* 1993, 684, indicated that the above-described method of Szymoniak et al. mainly produces geminally substituted compounds, which cannot be used as anionic ligands in metal complexes. Geminally substituted Cp compounds are not suitable for use as a ligand and are not considered to be within the scope of the invention.

Cyclopentadiene tetrasubstituted with methyl or ethyl groups and a substituent of the formula —RDR'$_n$, where R is a methylene or ethylene group and D is O, N or S, was disclosed in DE-A-43.03.647.

Bensley et al., *J. Org. Chem.* 1988, 53, 4417–4419, disclosed a tetramethyl-substituted cyclopentadiene containing a diphenylphos-phinyl group as the fifth substituent, which is coupled to the Cp via a propylene group.

Kresze et al., *Chemische Berichte* 1963, 666, 45–53, disclosed a bis(methoxyethyl)cyclopentadiene.

Hafner et al., *Chemische Berichte* 1963, 661, 52–75, disclosed a cyclopentadiene substituted with two adjacent methyl groups in combination with a dimethylamino group which is coupled to the Cp via a methylene group.

A tetramethyl-substituted cyclopentadiene containing an ethoxy group as the fifth substituent which is coupled to the Cp via a dimethylsilylene group was disclosed in EP-A-0,416,815.

A cyclopentadiene which is substituted with one tert-butyl group in addition to either a methoxy or an ethyl methoxy group was disclosed in Angew. *Chem. Int. Ed. Engl.* 1995, 34, 2266–2267.

Unexpectedly, it has now been found that catalyst components having high activity in the polymerization or copolymerization of α-olefins can be obtained if the Cp compounds of the invention are used singly as a ligand of a metal which is reduced. A mono-Cp-substituted metal complex with a metal in a reduced oxidation state is obtained; the Cp-containing ligand is multidentate and monoanionic. This has the advantage of strongly stabilizing the metal complex without blocking active sites of the complex, so that the complexes have excellent catalytic activity.

The metal is present in reduced form in the complex, which means that the metal is in a reduced oxidation state. As referred to herein, "reduced oxidation state" means an oxidation state which is lower than the highest possible oxidation state of the metal (for example, the reduced oxidation state is at most $M^{3+}$ for a transition metal of group 4, at most $M^{4+}$ for a transition metal of group 5 and at most $M^{5+}$ for a transition metal of group 6).

As referred to herein, a multidentate monoanionic ligand is bonded with a covalent bond to the reduced metal at one site (the anionic site) and is bonded either (i) with a coordinate bond to the reduced metal at one other site (bidentate) or (ii) with a plurality of coordinate bonds at several other sites (e.g., tridentate, tetradentate). Such coordinate bonding can take place, for example, via D heteroatom(s). It is noted, however, that heteroatom(s) can be present without coordinately bonding to the reduced metal, so long as at least one coordinate bond is formed between the electron-donating group D and the reduced metal.

As referred to herein, a coordinate bond is a bond (e.g., $H_3N$-$BH_3$) which when broken, yields either (i) two species without net charge and without unpaired electrons (e.g., $H_3N$: and $BH_3$) or (ii) two species with net charge and with unpaired electrons (e.g., $H_3N.^+$ and $BH_3.^-$). On the other hand, as referred to herein, a covalent bond is a bond (e.g., $CH_3$—$CH_3$) which when broken yields either (i) two species without net charge and with unpaired electrons (e.g., $CH_3$. and $CH_3$.) or (ii) two species with net charges and without unpaired electrons (e.g., $CH_3^+$ and $CH_3$:$^-$). A discussion of coordinate and covalent bonding is set forth in Haaland et al., *Angew. Chem (Int. Ed.)*, 1989, 28, 992.

The above-mentioned documents would not enable those skilled in the art to deduce that the compounds of the invention have the particular catalytic activity described above. Corresponding complexes in which the Cp compound is not substituted in the manner described in the present application prove unstable or, if they have been stabilized in some other way, are found to provide less active catalysts than the complexes containing substituted Cp compounds of the invention, particularly in the case of α-olefin polymerization or copolymerization.

Moreover, the Cp compounds of the invention are found to be able to stabilize highly reactive intermediaries such as organometal hydrides, organometal borohydrides, organometal alkyls and organometal cations. Furthermore they prove suitable as stable and volatile precursors for use in metal chemical vapour deposition.

SUMMARY OF THE INVENTION

A polysubstituted Cp compound refers to a cyclopentadiene substituted with at least a group of the formula —RDR'$_n$ and additionally with one to four $R^2$ groups to be defined hereinafter, hydrogen not being regarded as a substituent. Two of these $R^2$ groups may form a closed ring (e.g., a pyrrolidinyl group). Preferably, the polysubstituted Cp contains at least two $R^2$ groups as further substituents. Cp compounds thus substituted are found, when present as a ligand in a metal complex, to make the complex more suitable for the polymerization or copolymerization of α-olefins at high temperatures than complexes substituted with other Cp compounds.

The Cp compound may also be a heterocyclopentadiene compound. As referred to herein, the term "heterocyclopentadiene" group refers to a group which is derived from cyclopentadiene but in which at least one of the C atoms in the 5-ring thereof has been replaced by a hetero atom, which hetero atom can be selected from group 14, 15 or 16 of the Periodic Table of Elements. If more than one hetero atom is present in the 5-ring, these hetero atoms can be either identical or different. More preferably, the hetero atom is selected from group 15, and even more preferably the hetero atom is phosphorus. The ring of the heterocyclopentadiene may carry, depending on the number of hetero atoms h, 1 to (4-h) substituents $R^2$.

The $R^2$ groups may each, separately, be hydrogen or a hydrocarbon radical containing 1–20 carbon atoms (e.g., alkyl, aryl, aralkyl, and the like, including straight chain, branched, cyclic, and derivatives thereof). Examples of such hydrocarbon radicals are methyl, ethyl, propyl, butyl, hexyl, decyl, phenyl, benzyl, and p-tolyl. Alternatively, two hydrocarbon radicals situated next to one another can be linked to each other in a ring system; $R^2$ may also be a substituent which in addition to, or instead of, carbon and/or hydrogen contains one or more hetero atoms from groups 14 and/or 17 of the Periodic Table of Elements, a hetero atom not being bound directly to the Cp. Thus, a substituent may be a F- or Si-containing group, $R^2$ must not be a cyclopentadienyl group or a group derived therefrom.

The R group is the link between the Cp and the $DR'_n$ group. The shortest link between the Cp and D, referred to below as the main chain of R, is critical insofar as the accessibility of the $DR'_n$ group to the metal determines intramolecular coordination. The $DR'_n$ group may not coordinate effectively if the main chain of R is too short because of ring strain. Therefore, R has a length of at least one atom. The R group can be a hydrocarbon group containing 1–20 carbon atoms (e.g., alkylidene, arylidene, arylalkylidene and the like). Examples of such groups are methylene, ethylene, propylene, butylene, phenylene, with or without a substituted side chain (e.g., 1,1-dimethylethylene, 1,2-dimethylethylene, 1,1,2,2-tetramethyl-ethylene, 1-ethylpropylene, 1,1,2,2,4tetramethylbutylene). Preferably, the R group has the following structure:

where p=14 and E is an element from group 14 of the Periodic Table. The $R^3$ groups are as defined for $R^2$.

The main chain of the R group may consequently, in addition to carbon, also contain silicon or germanium. Examples of such R groups are: dialkylsilylene, dialkylgermylene, tetraalkyldisilylene or tetraalkylsilaethylene ($-SiR^3_2CR^3_2-$). The alkyl groups in such a group preferably contain 1–4 C atoms and are, more preferably, a methyl or ethyl group.

The $DR'_n$ group consists of a hetero atom D, selected from group 15 or 16 of the Periodic Table of Elements, and one or more R' bound to D. The number of R' groups (n) is determined by the type of hetero atom D, in the sense that n is 2 if D is from group 15, and that n is 1 if D is from group 16. Preferably, the hetero atom D is selected from the group consisting of nitrogen (N), oxygen (O), phosphorus (P) or sulphur (S); more preferably, the hetero atom is nitrogen (N). The R' groups may be identical or different and may be chosen from the same groups as defined for $R^2$ with the exception of hydrogen. Preferably, the R' group is an alkyl, more preferably an n-alkyl group containing 1–20 C atoms. More preferably, the R' group is an n-alkyl containing 1–10 C atoms. Another possibility is for two R' groups in the $DR'_n$ group to be joined together to give a ring-shaped structure. The $DR'_n$ group can be coordinated to the metal.

If used as the only Cp-containing ligand in a metal complex in which the metal is in a reduced oxidation state, the polysubstituted Cp compounds are found to provide compounds having good stability and good catalytic activity. The invention therefore also relates to said use and the metal complexes obtained.

Metal complexes comprising at least one compound of the invention as a ligand and a metal from groups 4–10 of the Periodic Table of Elements and rare earth elements (unless otherwise stated, references herein to the Periodic Table of Elements are to the new IUPAC notation found on the inside cover of the *Handbook of Chemistry* and *Physics,* 70th Ed., 1989/1990) are catalytically active. In this context, complexes of metals from groups 4 and 5 are preferably used as a catalyst component for polymerizing olefins, complexes of metals from groups 6 and 7 for metathesis and ring-opening metathesis polymerizations, and complexes of metals from groups 8–10 for olefin copolymerizations with polar comonomers, hydrogenations and carbonylations. Particularly suitable for the polymerization of polyolefins are metal complexes in which the metal is selected from the group consisting of Ti, Zr, Hf, V and Cr.

As referred to herein, the term "olefins" refers to α-olefins, diolefins and other ethylenically unsaturated monomers. If the term "polymerization of olefins" is used, this refers both to the polymerization of a single type of olefinic monomer and to the copolymerization of two or more different olefins.

The invention therefore also relates to the disclosed metal complexes, in which the metal is in a reduced oxidation state, and to the use thereof as catalyst components, in particular for polymerization of olefins, linear as well as branched, and cyclic olefins and dienes which may or may not be conjugated, and mixtures thereof. Preferably, the metal is selected from the group consisting of Ti(II), Zr(III), Hf(III) and V(IV).

DETAILED DESCRIPTION OF THE INVENTION

The sequence in which the substituents are attached to the Cp depends on the types of $R^2$ and $RDR'_n$ groups. Sometimes it is possible first to attach the substituents $R^2$ to the Cp and then $RDR'_n$, and sometimes the inverse order is observed.

Cp compounds substituted with a number of $R^2$ groups may, for example, be prepared by reacting a halide of the substituting compound in a mixture of the Cp compound and an aqueous solution of a base, in the presence of a phase transfer catalyst. It is possible to use substantially equivalent quantities of the halogenated substituting compounds with respect to the Cp compound. An equivalent quantity is understood as a quantity in moles which corresponds to the desired substitution multiplicity, for example, two moles per mole of Cp compound if disubstitution with the substituent in question is intended.

Depending on the size and the associated steric hindrance of the compounds to be substituted, it is usually possible to obtain trisubstituted to pentasubstituted Cp compounds at most. If a reaction with tertiary halides is carried out, generally only trisubstituted Cp compounds can be obtained, whereas with primary and secondary halides, it is generally possible to achieve tetra- and even penta-substitution.

Substituents which can be attached by means of this method are, for example, alkyl groups, both linear and branched, and cyclic, alkenyl and aralkyl groups. It is also possible for these to contain, in addition to carbon and hydrogen, one or more hetero atoms from groups 14–17 of the Periodic Table of Elements (e.g., O, N, Si or F). Examples of suitable groups are methyl, ethyl, iso-propyl, sec-butyl, -pentyl, -hexyl and -octyl, (tert-)butyl and higher homologues, cyclohexyl, and benzyl.

The substituents are preferably used in the method in the form of their halides, and more preferably in the form of their bromides. If bromides are used, a smaller quantity of phase transfer catalyst is found to be sufficient, and a higher yield of the desired compound is achieved.

By this method it is also possible, without intermediate isolation or purification, to obtain Cp compounds which contain specific combinations of substituents. Thus, for example, disubstitution with a first halide can be carried out and then, in the same reaction mixture, a second, different halide can be added as a third substituent. This can be repeated, so that it is also possible to prepare Cp derivatives having three or more different substituents.

The substitution takes place in a mixture of the Cp compound and an aqueous solution of a base (i.e., alkali solution). The concentration of the base in the solution is in the range between about 20 wt % and about 80 wt %. Hydroxides of an alkali metal (e.g., K or Na) are suitable as the base. The base is present in an amount of about 5 to about 30 moles, preferably about 6 to about, 20 moles, per mole of Cp compound. It was found that the reaction time can be considerably shortened if the alkali solution is replaced during the reaction, for example, by first mixing the alkali solution with the other components of the reaction mixture and, after some time, removing the aqueous phase and replacing it by a fresh quantity of the alkali solution.

The substitution takes place at atmospheric or elevated pressure such as, for example, up to about 100 MPa. Suitable ranges of elevated pressure include about 25 MPa to about 100 MPa. Elevated pressures are preferred when volatile components are present.

The temperature at which the reaction takes place can vary between wide limits such as, for example, a range from about –20° C. to about 120° C., preferably a range between about 10° C. and about 50° C. The reaction may be initiated at room temperature, whereupon the temperature of the reaction mixture may rise as a result of heat liberated by the reaction.

The substitution takes place in the presence of a phase transfer catalyst which is able to transfer OH ions from the aqueous phase to the organic phase containing Cp and the substituting compound, the OH ions reacting in the organic phase with an H atom which can be removed from the Cp compound. Possible phase transfer catalysts which may be used are quaternary ammonium, phosphonium, arsonium, stibonium, bismuthonium, and tertiary sulphonium salts. More preferably, ammonium and phosphonium salts are used such as, for example, tricaprylmethylammonium chloride, commercially available as Aliquat 336 (Fluka AG, Switzerland; General Mills Co., USA) and Adogen 464 (Aldrich Chemical Co., USA). Compounds such as benzyltriethylammonium chloride (TEBA) or benzyltriethylammonium bromide (TEBA-Br), benzyltrimethylammonium chloride, benzyltrimethylammonium bromide or benzyltrimethylammonium hydroxide (Triton B), tetra-n-butylammonium chloride, tetra-n-butylammonium bromide, tetra-n-butylammonium iodide, tetra-n-butylammonium hydrogen sulphate or tetra-n-butylammonium hydroxide and cetyltrimethylammonium bromide or cetyltrimethylammonium chloride, benzyltributyl-, tetra-n-pentyl-, tetra-n-hexyl- and trioctylpropylammonium chlorides and their bromides are likewise suitable. Usable phosphonium salts include, for example, tributyl-hexadecylphosphonium bromide, ethyltriphenylphosphonium bromide, tetraphenylphosphonium chloride, benzyltriphenyl-phosphonium iodide and tetrabutylphosphonium chloride. Crown ethers and cryptands such as, for example, 15-crown-5, 18-crown-6, dibenzo-18-crown-6, dicyclohexano-18-crown-6, 4,7,13,16,21-pentaoxa-1,10-diazabicyclo[8.8.5]tricosane (Kryptofix 221), 4,7,13,18-tetraoxa-1 ,10-diazabicyclo[8.5.5]eicosane (Kryptofix 211) and 4,7,1 3,16,21 ,24-hexaoxa-1, 10-diazabicyclo[8.8.8]-hexacosane ("[2.2.2]") and its benzo derivative Kryptofix 222 B can be used as a phase transfer catalyst. Polyethers such as ethers of ethylene glycols can also be used as a phase transfer catalyst. Quaternary ammonium salts, phosphonium salts, phosphoric acid triamides, crown ethers, polyethers and cryptands can also be used on supports such as, for example, on a crosslinked polystyrene or another polymer. The phase transfer catalysts are used in an amount of about 0.01 to about 2, preferably about 0.05 to about 1, equivalents relative to the amount of Cp compound.

In carrying out the synthetic process, the components can be added to the reactor in various sequential orders.

After the reaction is complete, the aqueous phase containing the alkaline solution and the organic phase containing the Cp compound are separated. The Cp compound is then obtained from the organic phase by fractional distillation.

An alternative method of preparation for alkyl-substituted cyclopentadienes is via alkyl-substituted acetylenes with the aid of a titanium catalyst, as disclosed by C. M. Garner, *Tet. Lett.* 1994, 35, 2463. Tetraalkyl-substituted cyclopentadienes can also be synthesized by reaction of 2-lithium-2-alkenes with an ester, followed by a ring closure to give the cyclopentadiene derivative, as described by D. M. Bensley, *J. Org. Chem.* 1988, 53, 4417–4419. According to the above-described synthesis methods, however, only tetraalkyl-cyclopentadienes having four identical alkyl groups can be prepared.

From acetylenes it is also possible to prepare, with the aid of tetracarbonyl nickel, cyclopentenone derivatives. Reaction of the cyclopentenone with a metal alkyl reagent (e.g., an alkyllithium or a Grignard reagent), followed by abstraction of water results in a corresponding cyclopentadiene derivative. Via this route, however, only cyclopentadiene derivatives having four identical substituents can be synthesized, as described by B. Fell, *Chem. Ber.* 1976, 109, 2914. Cyclopentenones containing different alkyl substitutes can be synthesized by the Nazarov reaction, from α-β-unsaturated esters. The cyclopentenones can be converted into cyclopentadienes as described above. This reaction is disclosed by J. -M. Conia, *Bul. Soc. Chim. France* 1970, 8–9, 2992.

Cyclopentadiene derivatives can be converted into fulvenes, which can react with metal alkyl reagents to give more highly substituted cyclopentadiene derivatives, by adapting the procedures described by K. J. Stone, *J. Org. Chem.* 1984, 49, 1849.

The group of the formula —RDR'$_n$ is attached at a free position of the Cp compound previously substituted at one or more positions according to, for example, the following synthetic route.

A substituted Cp compound is first deprotonated by reaction with a base or an alkali metal such as, for example, sodium or potassium.

Suitable bases include, for example, organolithium compounds (R$^4$Li) or organomagnesium compounds (R$^4$MgX), where R$^4$ is an alkyl, aryl or aralkyl group, and X is a halide, for example, n-butyllithium or i-propylmagnesium chloride. Potassium hydride, sodium hydride, inorganic bases (e.g., NaOH and KOH), and alcoholates and amides of Li, K and Na can likewise be used as a base. Mixtures of the above-mentioned compounds can also be used.

This reaction can be carried out in a polar dispersant such as, for example, ether or dimethoxyethane. Examples of suitable ethers are tetrahydrofuran (THF) or dibutyl ether. Apolar solvents such as, for example, toluene, hexane or heptane, can likewise be employed.

In a second step of synthesis, the cyclopentadienyl anion formed reacts with a compound according to the formula (R'$_n$D—R—Y), (X—R—Y) or (X—R—Sul), in which R', n, D and R are as defined hereinabove, and Y is a halogen atom (X) or a sulphonyl group (Sul). Examples of halogen atoms X are chlorine, bromine and iodine. Preferably, the halogen atom X is a chlorine atom or bromine atom. The sulphonyl group has the formula —OSO$_2$R$^5$, in which R$^5$ is a hydrocarbon radical containing 1–20 carbon atoms such as, for example, alkyl, aryl, aralkyl, and the like, including straight chain, branched, cyclic, and derivatives thereof. Examples of such hydrocarbon radicals are butane, pentane, hexane, benzene, naphthalene. Instead of, or in addition to, carbon and/or hydrogen, R$^5$ may also contain one or more hetero atoms from groups 14–17 of the Periodic Table of Elements (e.g., N, O, Si or F). Examples of sulphonyl groups are: phenylmethanesulphonyl, benzenesulphonyl, 1-butanesulphonyl, 2,5-dichlorobenzenesulphonyl, 5-dimethylamino-1-naphthalenesulphonyl, pentafluorobenzenesulphonyl, p-toluene-sulphonyl, trichloromethanesulphonyl, trifluoromethanesulphonyl, 2,4,6-triisopropylbenzenesulphonyl, 2,4,6-trimethylbenzenesulphonyl, 2-mesitylenesulphonyl, methanesulphonyl, 4methoxy-benzenesulphonyl, 1-naphthalenesulphonyl, 2-naphthalenesulphonyl, ethanesulphonyl, 4-fluorobenzenesulphonyl and 1-hexadecane-sulphonyl. Preferably, the sulphonyl group is p-toluenesulphonyl or trifluoromethanesulphonyl.

If D is a nitrogen atom and Y is a sulphonyl group, the compound according to the formula (R'$_n$D—D—Y) is formed in situ by reaction of an aminoalcohol compound (R'$_2$NR—OH) with a base such as defined hereinabove (e.g., potassium or sodium), followed by reaction with a sulphonyl halide (Sul—X).

The second reaction step can likewise be carried out in a polar dispersant such as described for the first step.

The temperature at which the reactions are carried out is in a range between about –60° C. and about 80° C. Reactions with X—R—Sul, X—R—Y and with R'$_n$D—R—Y, in which Y is Br or I, are generally carried out at in a temperature range between about –20° C. and about 20° C. Reactions with R'$_n$D—R—Y, in which Y is Cl, are generally carried out at a higher temperature (a range between about 10° C. to about 80° C.). The upper limit for the temperature at which the reactions are carried out is determined by, among other things, the boiling point of the compound R'$_n$D—R—Y and that of the solvent used.

After the reaction with a compound according to the formula (X—R—Sul) or (X—R—Y), a further reaction is carried out with LiDR'$_n$ or HDR'$_n$ to replace X by a DR'$_n$ functionality. This reaction is carried out, optionally in the same dispersant as mentioned above, in a temperature range between about 20° C. to about 80° C.

In the course of this synthetic process it is possible, when substituted Cp compounds are being alkylated, for geminal products to be formed in part. A geminal substitution is a substitution in which the number of substituents increases by one but in which the number of substituted carbon atoms does not increase. The amount of geminal products formed is low if the synthesis is carried out starting from a substituted Cp compound having one substituent, and increases as the substituted Cp compound contains more substituents. In the presence of sterically large substituents of the substituted Cp compound, no or virtually no geminal products are formed. Examples of sterically large substituents are secondary or tertiary alkyl substituents.

The amount of geminal product formed is also low if the second step of the reaction is carried out under the influence of a Lewis base whose conjugated acid has a dissociation constant with a PK$_a$ of less than or equal to about –2.5. The PKa values are based on D. D. Perrin, *Dissociation Constants of Organic Bases in Aqueous Solution*, IUPAC, Butterworths, London 1965. The values are determined in aqueous H$_2$SO$_4$ solution. Ethers may be mentioned as an example of suitable weak Lewis bases.

If geminal products have been formed by the process disclosed in the present application, these products can be separated in a simple manner from the non-geminal products by converting the mixture of geminal and non-geminal substituted products into a salt, by reaction with potassium, sodium or a base, the salt then being washed with a dispersant in which the salt of the non-geminal products is insoluble or sparingly soluble. Bases which can be used include the compounds as mentioned above. Suitable dispersants are apolar dispersants such as alkanes or toluene. Examples of suitable alkanes are heptane and hexane.

Other bridge systems can be synthesized from (cyclopentadienyl)-dialkylsilyl halides. Reaction of the silyl halide with a nucleophile such as, for example, lithium-dialkylamides, -phosphides or -arsides results in a silyl-bridged system with a donor hetero atom. Disila-bridged systems can be synthesized in an analogous manner.

From fulvenes, bridged systems containing a donor hetero atom and one carbon atom in the bridge can be synthesized, as described by D. M. Bensley, *J. Org. Chem.* 1988, 53, 4417.

The synthesis of metal complexes containing the above-described specific Cp compounds as a ligand may take place according to the processes known per se for this purpose. The use of these Cp compounds does not require modification of said known processes.

The polymerization of a-olefins (e.g., ethylene, propylene, butene, hexene, octene, and mixtures thereof or combinations with dienes) can be carried out in the presence of metal complexes containing as a ligand, the cyclopentadienyl compounds of the invention. Particularly suitable for this purpose are complexes of transition metals, not in their highest valency state (i.e., a reduced oxidation state), in which only one cyclopentadienyl compound of the invention is present as a ligand, and in which the metal is cationic during polymerization. These polymerizations can be carried out in any manner known for this purpose, and the use of the metal complexes as a catalyst component does not require any significant modification of these processes.

It will be appreciated that the catalyst system may also be formed in situ if the components thereof are added directly to a polymerization reactor system and a solvent or diluent, including liquid monomer, is used in the polymerization reactor.

These reactions can be carried out in suspension, solution, emulsion, gas phase or as a bulk polymerization. Supported catalysts, metal complexes on a carrier material, may be also used.

An organometallic compound can be used as a cocatalyst, the metal being selected from group 1, 2, 12 or 13 of the Periodic Table of Elements. Examples include trialkylaluminum, alkylaluminum halides, alkylaluminoxanes (e.g., methylaluminoxanes), tris(penta-fluorophenyl) borane, dimethylanilinium tetra(pentafluorophenyl) borate or mixtures thereof. If an organometallic compound is the cocatalyst, the molar ratio of the cocatalyst relative to the transition metal complex is usually is in a range between about 1:1 to about 10,000:1, and preferably is in a range between about 1:1 to about 2,500:1. If a compound containing or yielding a noncoordinating or poorly coordinating anion is selected as cocatalyst, the molar ratio usually is in a range between about 1:100 to about 1,000:1, and preferably is in a range between about 1:2 to about 250:1.

The polymerizations are carried out at temperature ranges between about −50° C. and about +350° C., more particularly, a range between about 25° C. and about 250° C. Pressures used are generally in a range between about atmospheric pressure and about 250 MPa, for bulk polymerizations a pressure range between about 50 MPa and about 250 MPa is preferred, and for the remaining polymerization processes a pressure range between about 0.5 MPa and about 25 MPa is preferred. Dispersants and solvents that may be used include hydrocarbons such as pentane, heptane and mixtures thereof. Aromatic, optionally perfluorinated, hydrocarbons likewise may be used. The monomer to be employed in the polymerization can also be used as a dispersant or solvent.

As a person skilled in the art would be aware, the transition metal complex as well as the cocatalyst can be present in the catalyst composition as a single component or as a mixture of several components. For instance, a mixture may be desired where there is a need to influence the molecular properties of the polymer, such as molecular weight and in particular molecular weight distribution.

The products and methods of the invention have been disclosed in Dutch Patent Application No. 1003008, filed May 3, 1996, and international publication W096/13529, the entire contents of which are hereby incorporated by reference and relied upon. Moreover, all journal articles, texts and patents cited in this specification are incorporated by reference in their entirety.

The invention will be explained with reference to the following examples, but is not limited thereto.

Characterization of the products obtained involved the following analytical methods. Gas chromatography (GC) was carried out on a Hewlett-Packard 5890 series 11 with an HP crosslinked methyl silicon gum (25 m×0.32 mm×1.05 μm) column. Combined gas chromatography/mass spectrometry (GC-MS) was carried out with a Fisons MD800 equipped with a quadrupole mass detector, autoinjector Fisons AS800 and CPSil8 column (30 m×0.25 mm×1 μm, low bleed). NMR was carried out on a Bruker ACP200 ($^1$H-200 MHz; $^{13}$C-50 MHz) or Bruker ARX400 ($^1$H=400 MHz; $^{13}$C-100 MHz). To characterize metal complexes, use was made of a Kratos MS80 or alternatively a Finnigan Mat 4610 mass spectrometer.

EXAMPLE I

Preparation of di(2-propyl)cyclopentadiene

In a double-walled reactor having a volume of 200 mL, provided with baffles, condenser, top stirrer, thermometer and dropping funnel, 180 g of clear 50% strength NaOH (2.25 mol), 9.5 g of Aliquat 336 (23 mmol) and 15 g (0.227 mol) of freshly cracked cyclopentadiene were combined. The reaction mixture was stirred vigorously at a speed of 1385 rpm for a few minutes, then 56 g of 2-propyl bromide (0.46 mol) were added. The reaction mixture was then cooled with circulating water at 10° C. A few minutes after the addition of the 2-propyl bromide, the temperature rose by approximately 10° C. Stirring then continued for 6 hours at 50° C. GC was used to show that 92% of the mixture of di- and tri(2-propyl)cyclopentadiene was disubstituted cyclopentadiene. The product was distilled at 10 mbar and 70° C. After distillation, 25.35 g of di(2-propyl) cyclopentadiene were obtained, which was characterized with GC, GC-MS, $^{13}$C— and $^1$H-NMR.

EXAMPLE II

Preparation of tri(2-propyl)cyclopentadiene

In a double-walled reactor having a volume of 200 mL, provided with baffles, condenser, top stirrer, thermometer and dropping funnel, 180 g of clear 50% strength NaOH (2.25 mol), 9.5 g of Aliquat 336 (23 mmol) and 15 g (0.227 mol) of freshly cracked cyclopentadiene were combined. The reaction mixture was stirred vigorously at a speed of 1385 rpm for a few minutes, then 84 g of 2-propyl bromide (0.68 mol) were added. The reaction mixture was then cooled with circulating water at 10° C. A few minutes after the addition of the 2-propyl bromide, the temperature rose by approximately 10° C. GC was used to show that approximately 30 minutes after the addition of all the 2-propyl bromide, monosubstituted 2-propylcyclopentadiene had been formed. The reaction mixture was then heated to 50° C. After two hours, stirring was stopped and phase separation was performed. The aqueous layer was drawn off, and 180 g (2.25 mol) of fresh 50% strength NaOH were added. Stirring then continued for one hour at 50° C. GC was used to show that between 90% and 95% of the mixture of di-, tri- and tetra-(2-propyl)cyclopentadiene was trisubstituted cyclopentadiene. The product was distilled at 1.3 mbar and 77–78° C. After distillation, 31.9 g of tri(2-propyl) cyclopentadiene were obtained, which was characterized with GC, GC-MS, $^{13}$C- and $^1$H-NMR.

EXAMPLE III

Preparation of tetra(2-propyl)cyclopentadiene

Analogous to Example II, but now 114 g of 2-propyl bromide (0.93 mol) were added, and after 7 hours, the aqueous layer was replaced a second time and a further 5 g (12 mmol) of Aliquat 336 were added. Stirring then took place for 16 hours at 55° C. GC was used to show that 85% of the mixture of tri- and tetra(2-propyl)cyclopentadiene was tetrasubstituted cyclopentadiene. The product was distilled at 1.0 mbar and 88–90° C. After distillation, 34.9 g of tetra(2-propyl)cyclopentadiene were obtained, which was characterized with GC, GC-MS, $^{13}$C- and $^1$H-NMR.

EXAMPLE IV

Preparation of di(cyclohexyl)cyclopentadiene

A double-walled reactor having a volume of 1 L, provided with baffles, condenser, top stirrer, thermometer and dropping funnel, was charged with 600 g of clear 50% strength NaOH (7.5 mol), followed by cooling to 8° C. Then 20 g of Aliquat 336 (49 mmol) and 33 g (0.5 mol) of freshly cracked cyclopentadiene were added. The reaction mixture was stirred vigorously for a few minutes, then 172 g of cyclohexyl bromide (1.05 mol) were added. The reaction mixture was then cooled with circulating water at 10° C. After two hours of stirring at room temperature, the reaction mixture was heated to 70° C., followed by a further 6 hours of stirring. GC was used to show that 79% of the mixture of mono-, di- and tri-(cyclohexyl)cyclopentadiene was disubstituted cyclopentadiene. The product was distilled at 0.04 mbar and 110–120° C. After distillation, 73.6 g of di(cyclohexyl)cyclopentadiene were obtained, which was characterized with GC, GC-MS, $^{13}$C- and $^1$H-NMR.

EXAMPLE V
Preparation of di- and tri(3-pentyl)cyclopentadiene

A double-walled reactor having a volume of 1 L, provided with baffles, condenser, top stirrer, thermometer and dropping funnel, was charged with 430 g (5.4 mol) of clear 50% strength NaOH. Then 23 g of Aliquat 336 (57 mmol) and 27 g (0.41 mol) of freshly cracked cyclopentadiene were added. The reaction mixture was stirred vigorously for a few minutes, then 150 g of 3-pentyl bromide (1.0 mol) were added over a period of one hour, while the reaction mixture was cooled with circulating water at 10° C. After one hour of stirring at room temperature, the reaction mixture was heated to 70° C., followed by a further three hours of stirring. Stirring was stopped and phase separation was performed. The aqueous layer was drawn off and 540 g (6.70 mol) of fresh 50% strength NaOH were added, followed by a further 4 hours of stirring at 70° C. GC was used to show that the mixture consisted of di- and tri(3-pentyl) cyclopentadiene in a ratio of approximately 3:2, respectively. The products were distilled at 0.2 mbar, 51° C. and 0.2 mbar, 77–80° C., respectively. After distillation, 32 g of di- and 18 g of tri(3-pentyl)cyclopentadiene were obtained, which were characterized with GC, GC-MS, $^{13}$C- and $^1$H-NMR.

EXAMPLE VI
Preparation of tri(cyclohexyl)cyclopentadiene

A double-walled reactor having a volume of 1 L, provided with baffles, condenser, top stirrer, thermometer and dropping funnel, was charged with 600 g of clear 50% strength NaOH (7.5 mol), followed by cooling to 8° C. Then 20 g of Aliquat 336 (49 mmol) and 33 g (0.5 mol) of freshly cracked cyclopentadiene were added. The reaction mixture was stirred vigorously for a few minutes, then 256 g of cyclohexyl bromide (1.57 mol) were added, while the reaction mixture was cooled with circulating water at 10° C. After one hour of stirring at room temperature, the reaction mixture was heated to 70° C., followed by a further two hours of stirring. After two hours, stirring was stopped and phase separation was performed. The aqueous layer was drawn off and 600 g (7.5 mol) of fresh 50% strength NaOH were added, followed by a further 4 hours of stirring at 70° C. GC was used to show that the mixture comprised 10% of di- and 90% of tri(cyclohexyl)cyclopentadiene. The product was distilled at 0.04 mbar and 130° C. After distillation, 87.4 g of tri(cyclohexyl)cyclopentadiene were obtained, which was characterized with GC, GC-MS, $^{13}$C- and $^1$H-NMR.

EXAMPLE VII
Preparation of di(2-butyl)cyclopentadiene

A double-walled reactor having a volume of 1 L, provided with baffles, condenser, top stirrer, thermometer and dropping funnel, was charged with 600 g of clear 50% strength NaOH (7.5 mol), followed by cooling to 10° C. Then 30 g of Aliquat 336 (74 mmol) and 48.2 g (0.73 mol) of freshly cracked cyclopentadiene were added. The reaction mixture was stirred vigorously for a few minutes, then 200 g of 2-butyl bromide (1.46 mol) were added over a period of half an hour, while the reaction mixture was cooled with circulating water at 10° C. After two hours of stirring at room temperature, the reaction mixture was heated to 60° C., followed by a further 4 hours of stirring. GC was used to show that more than 90% of the substituted cyclopentadienes was di(2-butyl)cyclopentadiene. The product was distilled at 20 mbar and 80–90° C. After distillation, 90.8 g of di(2-butyl)cyclopentadiene were obtained, which was characterized with GC, GC-MS, $^{13}$C- and $^1$H-NMR.

EXAMPLE VIII
Preparation of tri(2-butyl)cyclopentadiene

A double-walled reactor having a volume of 1 L, provided with baffles, condenser, top stirrer, thermometer and dropping funnel, was charged with 400 g of clear 50% strength NaOH (5 mol). Then 9.6 g of Aliquat 336 (24 mmol) and 15.2 g (0.23 mol) of freshly cracked cyclopentadiene were added. The reaction mixture was stirred vigorously for a few minutes, then 99.8 g of 2-butyl bromide (0.73 mol) were added over a period of half an hour, while the reaction mixture was cooled with circulating water at 10° C. After half an hour's stirring at room temperature, the reaction mixture was heated to 70° C., followed by a further three hours of stirring. Stirring was stopped and phase separation was performed. The aqueous layer was drawn off and 400 g (5.0 mol) of fresh 50% strength NaOH were added, followed by a further two hours of stirring at 70° C. GC was used to show that more than 90% of the mixture of di-, tri- and tetra(2-butyl)cyclopentadiene was trisubstituted cyclopentadiene. The product was distilled at 1 mbar and 91° C. After distillation, 40.9 g of tri(2-butyl)cyclopentadiene were obtained, which was characterized with GC, GC-MS, $^{13}$C- and $^1$H-NMR.

EXAMPLE IX
Preparation of di- and tri(2-pentyl)cyclopentadiene

A double-walled reactor having a volume of 1 L, provided with baffles, condenser, top stirrer, thermometer and dropping funnel, was charged with 900 g (11.25 mol) of clear 50% strength NaOH. Then 31 g of Aliquat 336 (77 mmol) and 26.8 g (0.41 mol) of freshly cracked cyclopentadiene were added. The reaction mixture was stirred vigorously for a few minutes, then 155 g of 2-pentyl bromide (1.03 mol) were added over a period of one hour, while the reaction mixture was cooled with circulating water at 10° C. After three hours of stirring at room temperature, the reaction mixture was heated to 70° C., followed by a further two hours of stirring. Stirring was stopped and phase separation was performed. The aqueous layer was drawn off and 900 g (11.25 mol) of fresh 50% strength NaOH were added, followed by a further two hours of stirring at 70° C. GC was used to show that at that instant the mixture consisted of di- and tri(2-pentyl)cyclopentadiene in a ratio of approximately 1:1. The products were distilled at 2 mbar, 79–81° C. and 0.5 mbar, 102° C., respectively. After distillation, 28 g of di- and 40 g of tri(2-pentyl)cyclopentadiene were obtained, which were characterized with GC, GC-MS, $^{13}$C- and $^1$H-N MR.

EXAMPLE X
Preparation of di (2-propyl)cyclohexylcyclopentadiene

In a double-walled reactor having a volume of 200 mL, provided with baffles, condenser, top stirrer, thermometer and dropping funnel, 150 g of clear 50% strength NaOH (1.9 mol), 7 g of Aliquat 336 (17.3 mmol) and 8.5 g (0.13 mol) of freshly cracked cyclopentadiene were combined. The reaction mixture was stirred vigorously at a speed of 1385 rpm for a few minutes, then 31.5 g of 2-propyl bromide (0.26 mol) were added, while the reaction mixture was cooled with circulating water at 10° C. Metering in took a total time of one hour. After addition of the bromide, the reaction mixture was heated to 50° C. After two hours, stirring was stopped and phase separation was performed. The aqueous layer was drawn off, and 150 g (1.9 mol) of fresh 50% strength NaOH were added. This was followed by the addition of 20.9 g (0.13 mol) of cyclohexyl bromide, and stirring then continued for a further three hours at 70° C. GC was used to show that 80% of the substituted cyclopentadienes was di(2-propyl)cyclohexylcyclopentadiene. The product was distilled at 0.3 mbar and 80° C. After distillation, 17.8 g of di(2-propyl)cyclohexyl-cyclopentadiene were obtained, which was characterized with GC, GC-MS, $^{13}$C- and $^1$H-NMR.

EXAMPLE XI

Preparation of tetra(octyl)cyclopentadiene

A double-walled reactor having a volume of 1.5 L, provided with baffles, condenser, top stirrer, thermometer and dropping funnel, was charged with 900 g of clear 50% strength NaOH (11.3 mol), followed by cooling to 10° C. Then 30 g of Aliquat 336 (74 mmol) and 48 g (0.72 mol) of freshly cracked cyclopentadiene were added. The reaction mixture was stirred vigorously for a few minutes, then 577 g of octyl bromide (2.99 mol) were added over a period of one hour, while the reaction mixture was cooled with circulating water at 10° C. After one hour of stirring at room temperature, the reaction mixture was heated to 35° C., followed by a further 6 hours of stirring. Stirring was stopped and phase separation was performed. The aqueous layer was drawn off and 920 g (11.5 mol) of fresh 50% strength NaOH were added, followed by a further 5 hours of stirring at room temperature. GC was used to show that 10% of tri-, 83% of tetra- and 7% of penta(octyl)cyclopentadiene were present in the mixture. The product was distilled under reduced pressure. After vacuum distillation, 226.6 g of tetra(octyl)cyclopentadiene were obtained, which was characterized with GC, GC-MS, $^{13}$C- and $^1$H-NMR.

EXAMPLE XII

Preparation of tetra(n-propyl)cyclopentadiene

A double-walled reactor having a volume of 1 L, provided with baffles, condenser, top stirrer, thermometer and dropping funnel, was charged with 1000 g of clear 50% strength NaOH (12.5 mol), followed by cooling to 10° C. Then 30 g of Aliquat 336 (74 mmol) and 50 g (0.75 mol) of freshly cracked cyclopentadiene were added. The reaction mixture was stirred vigorously for a few minutes, then 373 g of propyl bromide (3.03 mol) were added over a period of one hour, while the reaction mixture was cooled with circulating water at 10° C. After one hour of stirring at room temperature, the reaction mixture was heated to 35° C., followed by a further 6 hours of stirring. Stirring was stopped and phase separation was performed. The aqueous layer was drawn off and 990 g (12.4 mol) of fresh 50% strength NaOH were added, followed by a further 5 hours of stirring at room temperature. GC was used to show that 14% of tri-, 80% of tetra- and 6% of penta(propyl) cyclopentadiene were present in the mixture. The product was distilled under reduced pressure. After vacuum distillation, 103.1 g of tetra(propyl)cyclopentadiene were obtained, which was characterized with GC, GC-MS, $^{13}$C- and $^1$H-NMR.

EXAMPLE XIII

Preparation of di(2-phenyl-propyl)cyclopentadiene

A double-walled reactor having a volume of 1 L, provided with baffles, condenser, top stirrer, thermometer and dropping funnel, was charged with 600 g of clear 50% strength NaOH (7.5 mol), followed by cooling to 8° C. Then 20 g of Aliquat 336 (49 mmol) and 33 g (0.5 mol) of freshly cracked cyclopentadiene were added. The reaction mixture was stirred vigorously for a few minutes, then 219 g of 1-bromo-2-phenylpropane (1.1 mol) were added all at once, while the reaction mixture was cooled with circulating water at 10° C. After two hours of stirring at room temperature, the reaction mixture was heated to 70° C., followed by a further 6 hours of stirring. GC was used to show that 89% of the substituted cyclopentadienes was di(2-phenyl-propyl)cyclopentadiene. The product was distilled at low pressure and high temperature, whereupon 95.34 g (0.4 mol; 80%) of di(2-phenyl-propyl)cyclopentadiene were obtained, which was characterized with GC, GC-MS, $^{13}$C- and $^1$H-NMR.

EXAMPLE XIV

Preparation of di(1,1-dimethylpropyl)cyclopentadiene

A double-walled reactor having a volume of 1 L, provided with baffles, condenser, top stirrer, thermometer and dropping funnel, was charged with 600 g of clear 50% strength NaOH (7.5 mol), followed by cooling to 8° C. Then 20 g of Aliquat 336 (49 mmol) and 33 g (0.5 mol) of freshly cracked cyclopentadiene were added. The reaction mixture was stirred vigorously for a few minutes, then 226.6 g of 2-bromo-2-methylbutane (1.5 mol) were added all at once, while the reaction mixture was cooled with circulating water at 10° C. After two hours of stirring at room temperature, the reaction mixture was heated to 70° C., followed by a further 6 hours of stirring. GC was used to show that 56% of the substituted cyclopentadienes was di(1,1-dimethyl-propyl) cyclo-pentadiene. The product was distilled at low pressure and high temperature, whereupon 47.7 g (0.23 mol; 46%) of di(1,1dimethyl-propyl)cyclopentadiene were obtained, which was characterized with the aid of GC, GC-MS, $^{13}$C- and $^1$H-NMR.

EXAMPLE XV

Preparation of di(1-methyl-i-ethyl-propl)cyclopentadiene

This preparation was carried out as in the preceding example, but now with: 247.6 g of 3-bromo-3-methylpentane. GC was used to show that 55% of the substituted cyclopentadienes was di(1-methyl-1-ethyl-propyl)cyclopentadiene, and after distillation 50.4 g (43%) of di(1-methyl-1-ethyl-propyl)cyclopentadiene were obtained.

EXPERIMENT XVI

In-situ preparation of 2-(N,N-dimethylaminoethyl) tosylate

Under dry nitrogen, a solution of n-butyllithium in hexane (one equivalent) in dry tetrahydrofuran was added (metering time: 60 minutes) at −10° C. to a solution of 2-dimethyl-aminoethanol (one equivalent) in a three-necked round-bottomed flask provided with a magnetic stirrer and a dropping funnel. After the addition of all the butyllithium, the mixture was brought to room temperature and stirred for two hours. Subsequently the mixture was cooled (−10° C.) and p-toluenesulphonyl chloride (one equivalent) was then added, followed by 15 minutes of stirring at this temperature, before the solution was added to a cyclopentadienyl anion.

By a similar method, comparable tosylates can be prepared. In a number of the following examples, a tosylate is in each case coupled with alkylated Cp compounds. In the course of said coupling, the required substitution reaction is accompanied by geminal coupling. In almost all cases, it was possible to separate the geminal isomers from the non-geminal isomers by conversion of the non-geminal isomers into their sparingly soluble potassium salt, followed by this salt being washed with a solvent in which said salt is insoluble or sparingly soluble.

EXAMPLE XVII a. Preparation of (dimethylaminoethyl) dicyclohexylcyclopentadiene Under a nitrogen atmosphere, a solution of n-butyllithium in hexane (18.7 mL; 1.6 mol/L; 30 mmol) was added dropwise to a cooled (0° C.) solution of dicyclohexyl-cyclopentadiene (Example IV) (6.90 g; 30.0 mmol) in dry tetrahydrofuran (125 ml) in a 250 mL three-necked round-bottomed flask provided with a magnetic stirrer and a dropping funnel. After 24 hours of stirring at room temperature, 30.0 mmol of 2-dimethylaminoethyl tosylate prepared in situ were added. After 18 hours of stirring, the conversion was found to be 88%, and water (100 ml) was carefully added dropwise to the reaction mixture and the tetrahydrofuran was then distilled off. The crude product was extracted with ether, and the combined organic phase was then dried with sodium sulphate, and evaporated to dryness. The residue was purified on a silica gel column, which resulted in 7.4 g of (dimethylaminoethyl) dicyclohexylcyclo-pentadiene.

b. Synthesis of 1-(dimethylaminoethyl)-2,4-dicyclohexylcyclopentadienyltitanium(III) dichloride and [1-(dimethylaminoethyl)-2,4-dicyclohexylcyclopentadienyl]methyl-titanium(III)

[$C_5H_2(c-C_6H_{11})_2(CH_2)_2NMe_2Ti(III)Cl_2$] and [$C_5H_2(c-C_6H_{11})_2(CH_2)_2NMe_2Ti(III)Me_2$]

In a Schlenk vessel, 1.37 g (4.54 mmol) of (dimethylaminoethyl)dicyclohexylcyclopentadiene were dissolved in 30 mL of diethyl ether and the solution was then cooled to −60° C. Then 2.84 mL of n-butyllithium (1.6 M in hexane; 4.54 mmol) were added dropwise. The reaction mixture was slowly brought to room temperature, followed by stirring for two hours. After evaporation of the solvent, a yellow powder remained to which 30 mL of petroleum ether were added.

In a second Schlenk vessel, 40 mL of tetrahydrofuran were added to 1.68 g of Ti(III)Cl$_3$.3THF (4.53 mmol).

Both Schlenk vessels were cooled to 60° C. and the organolithium compound was then added to the Ti(III)Cl$_3$ suspension. The reaction mixture was then stirred for 18 hours at room temperature, after which the solvent was evaporated. To the residue, 50 mL of petroleum ether were added, which was subsequently evaporated to dryness. A green solid remained containing 1-(di-methylaminoethyl)-2,4-dicyclohexylcyclopentadienyltitanium(III) dichloride.

In a Schlenk vessel, 0.31 g (0.671 mmol) of the above-described 1-(dimethylaminoethyl)-2,4-dicyclohexylcyclopentadienyltitanium(III) dichloride was dissolved in 30 mL of diethyl ether. The solution was cooled to −60° C. and 0.73 mL (1.84 M in diethyl ether; 1.34 mmol) of methyllithium was then added dropwise. The solution was slowly brought to room temperature, followed by stirring for one hour. Then the solvent was evaporated and the residue extracted with 40 mL of petroleum ether. The filtrate was boiled down and dried for 18 hours in vacuo. There remained 0.14 g of a black/brown oil containing [1-(dimethylaminoethyl)-2,4-dicyclohexylcyclopentadienyl]dimethyltitanium(III).

EXAMPLE XVIII a. Preparation of (dimethylaminoethyl)di(2-pentyl) cyclopentadiene Under a nitrogen atmosphere, a solution of n-butyllithium in hexane (24.0 ml; 1.6 mol/L; 38 mmol) was added dropwise to a cooled (0° C.) solution of di-(2-pentyl) cyclopentadiene (7.82 g; 38.0 mmol) in dry tetrahydrofuran (125 ml) in a 250 mL three-necked round-bottomed flask provided with a magnetic stirrer and a dropping funnel. After 24 hours of stirring at room temperature, 2-dimethylaminoethyl tosylate (38.0 mmol) prepared in situ was added. After 18 hours of stirring, the conversion was found to be 92%, and water (100 ml) was carefully added dropwise to the reaction mixture and the tetrahydrofuran was then distilled off. The crude product was extracted with ether, and the combined organic phase was then dried with sodium sulphate, and evaporated to dryness. The residue was purified on a silica gel column, which resulted in 8.2 g of (dimethylaminoethyl)-di(2-pentyl)cyclopentadiene.

b. Synthesis of 1-(dimethylaminoethyl)-2,4-di(2-pentyl)-cyclopentadienyltitanium(III) dichloride and [1-(dimethylaminoethyl)-2,4-di(2-pentyl)cyclopentadienyl] dimethyltitanium(III)

[$C_5H_2(2-C_5H_{11})_2(CH_2)_2NMe_2Ti(III)Cl_2$] and
[$C_5H_2(2-C_5H_{11})_2(CH_2)_2NMe_2Ti(III)Me_2$]

In a Schlenk vessel, 1.60 g (5.77 mmol) of (dimethylaminoethyl)di(2-pentyl)cyclopentadiene were dissolved in 40 mL of diethyl ether and the solution was then cooled to −60° C. Then 3.6 mL of n-butyllithium (1.6 M in hexane; 5.77 mmol) were added dropwise. The reaction mixture was slowly brought to room temperature, followed by stirring for two hours.

In a second Schlenk vessel, 40 mL of tetrahydrofuran were added to 2.14 g of Ti(III)Cl$_3$.3THF (5.77 mmol).

Both Schlenk vessels were cooled to −60° C. and the organolithium compound was then added to the Ti(III)Cl$_3$ suspension. The reaction mixture was then stirred for 18 hours at room temperature, after which the solvent was evaporated. To the residue, 50 mL of petroleum ether were added, which was subsequently evaporated to dryness. 1.60 g of a green solid remained containing 1-(dimethylaminoethyl)-2,4-di(2-pentyl) cyclopentadienyltitanium(III) dichloride.

In a Schlenk vessel, 0.33 g (0.835 mmol) of 1-(dimethyl-aminoethyl)di(2-pentyl)cyclopentadienyltitanium(II) dichloride was dissolved in 40 mL of diethyl ether. The solution was cooled to −60° C. and 0.90 mL of methyllithium (1.84 M in diethyl ether; 1.66 mmol) was then added dropwise. The reaction mixture was slowly brought to room temperature, followed by stirring for one hour. Then the solvent was evaporated. The residue was extracted with 50 mL of petroleum ether, and the filtrate was then boiled down. There remained 0.24 g of a black/brown oil containing [1-(dimethyl-aminoethyl)-2,4-di(2-pentyl) cyclopentadienyl]-dimethyltitanium(III).

EXAMPLE XIX a. Preparation of (dimethylaminoethyl)tri(2-propyl) cyclopentadiene In a dry 500 mL three-necked flask with a magnetic stirrer, a solution of 62.5 mL of n-butyllithium (1.6 M in n-hexane; 100 mmol) was added under a dry nitrogen atmosphere to a solution of 19.2 g (100 mmol) of triisopropyl-cyclopentadiene in 250 mL of tetrahydrofuran at −60° C. After heating to room temperature (in approximately one hour) stirring continued for a further two hours. After cooling to −60° C., a solution of dimethylaminoethyl tosylate (105 mmol) prepared in situ was added over a period of 5 minutes. The reaction mixture was heated to room temperature, followed by overnight stirring. After addition of water, the product was extracted with petroleum ether (40–60° C.). The combined organic layer was dried with sodium sulphate, and evaporated under reduced pressure. The conversion was greater than 95%. The yield of product after distillation (based on triisopropyl-cyclopentadiene) was approximately 55%.

b. Synthesis of [1-(dimethylaminoethyl)-2,3,5-tri(2-propyl) cyclopentadienyltitanium(III) dichloride and [1-(dimethylaminoethyl)-2,3,5-tri(2-propyl)cyclopentadienyl]-dimethyltitanium(III)

[C$_5$H(iPr)$_3$(CH$_2$)$_2$NMe$_2$Ti(III)Cl$_2$] and
[C$_5$H(iPr)$_3$(CH$_2$)$_2$NMe$_2$Ti(III)Me$_2$]

In a 500 mL 3-necked flask, 200 mL of petroleum ether were added to 8.5 g (28.18 mmol) of potassium 1-(dimethylaminoethyl)-2,3,5-tri(2-propyl)cyclopentadienyl. In a second (1 L) 3-necked flask, 300 mL of tetrahydrofuran were added to 10.5 g (28.3 mmol) of Ti(III)Cl$_3$.3THF. Both flasks were cooled to −60° C. and the organopotassium compound was then added to the Ti(III)Cl$_3$ suspension. The reaction mixture containing 1-(dimethylaminoethyl)-2,3,5-tri(2-propyl) cyclopentadienyltitanium(III) dichloride was slowly brought to room temperature, after which stirring was continued for a further 18 hours. This was followed by cooling to −60° C. and 30.6 mL of methyllithium (1.827 M in diethyl ether, 55.9 mmol) were then added. After two hours of stirring at room temperature, the solvent was removed and the residue was dried in vacuo for 18 hours. To the product, 700 mL of petroleum ether were then added, followed by filtration. The filtrate was boiled down and dried in vacuo for two days. There remained 9.2 g of a brown/black oil containing [1-(dimethylaminoethyl)-2,3,5-tri(2-propyl) cyclopenta-dienyl]dimethyl-titanium(III).

EXAMPLE XX a. Preparation of (di-n-butylaminoethyl)di(2-pentyl) cyclopentadiene

The reaction was carried out in a manner analogous to that for (dimethylaminoethyl)di(2-pentyl)cyclopentadiene, the tosylate of N,N-di-n-butylaminoethanol being prepared in situ. The conversion was 88%. After preparative column purification on silica gel using, successively, petroleum ether (40–60° C.) and tetrahydrofuran, followed by distillation under reduced pressure, di-(n-butyl-aminoethyl)di(2-pentyl) cyclopentadiene was obtained in a yield of 51%.

b. Preparation of 1-(di-n-butylaminoethyl)-2,4-di(2-pentyl) cyclopentadienyltitanium(III) dichloride

[C$_5$H$_2$(2-C$_5$H$_{11}$)$_2$(CH$_2$)$_2$N(n-C$_4$H$_9$)$_2$Ti(III)Cl$_2$]

In a Schlenk vessel, 0.919 g (2.54 mmol) of (di-n-butylaminoethyl)di(2-pentyl)cyclopentadiene was dissolved in 40 mL of diethyl ether and the solution was then cooled to −60° C. 1.6 mL of n-butyllithium (1.6 M in hexane; 2.56 mmol) was then added dropwise. The reaction mixture was slowly brought to room temperature, followed by two hours of stirring. This was then added, at −60° C., to 960 mg (2.59 mmol) of Ti(III)Cl$_3$.3THF in 20 mL of tetrahydrofuran. The reaction mixture was then stirred for 18 hours at room temperature, after which the solvent was evaporated. The residue was washed with 10 mL. There remained 0.95 g of a green solid containing 1-(di-n-butylaminoethyl)-2,4-di(2-pentyl)-cyclopentadienyltitanium(III) dichloride.

EXAMPLE XXI a. Preparation of (dimethylaminoethyl)di(2-propyl) cyclopentadiene

The reaction was carried out in a manner analogous to that for (dimethylaminoethyl)tri(2-propyl)cyclopentadiene. The conversion was 97%. The dimethylaminoethyldiisopropylcyclopentadiene was obtained by distillation, with a yield of 54%.

b. Synthesis of [1-(dimethylaminoethyl)-2,4-di(2-propyl)-cyclopentadienyltitanium(III) dichloride and 1-(dimethylaminoethyl)-2,4-di(2-propyl)cyclopentadienyl] dimethyltitanium(III)

[C$_5$H$_2$(iPr)$_2$(CH$_2$)$_2$NMe$_2$Ti(III)Cl$_2$] and
[C$_5$H$_2$(iPr)$_2$(CH$_2$)$_2$NMe$_2$Ti(III)Me$_2$]

To 8.9 g (40.3 mmol) of (dimethylaminoethyl)di(2-propyl)cyclopentadiene in 100 mL of tetrahydrofuran in a 250 mL 3-necked flask, 25.2 mL of n-butyllithium (1.6 M, 40.3 mmol) were added dropwise. In a second (500 mL) 3-necked flask, 100 mL of tetrahydrofuran were added to 14.93 g (40.3 mmol) of Ti(III)Cl$_3$.3THF. Both flasks were cooled to −60° C. and the organolithium compound was then added to the Ti(III)Cl$_3$ suspension. The reaction mixture containing 1-(dimethylaminoethyl)-2,4-di(2-propyl) cyclopentadienyltitanium(III) dichloride was slowly brought to room temperature, after which stirring was continued for a further 18 hours. This was followed by cooling to −60° C., and 50.4 mL of methyllithium (1.6 M in diethyl ether; 80.6 mmol) were then added. After two hours of stirring at room temperature, the solvent was removed and the residue was dried in vacuo for 18 hours. To the product, 350 mL of petroleum ether were then added, followed by filtration. The filtrate was boiled down and dried in vacuo for one day. There remained 11.6 g of a brown/black oil containing [1-(dimethylaminoethyl)-2,4-di(2-propyl) cyclopentadienyl]-dimethyltitanium(III).

EXAMPLE XXII a. Preparation of (dimethylaminoethyl)di(2-butyl) cyclopentadiene

Under a nitrogen atmosphere, a solution of n-butyllithium in hexane (31.2 ml; 1.6 mol/L; 50 mmol) was added dropwise to a cooled (0° C.) solution of di-(2-butyl) cyclopentadiene (8.90 g; 50.0 mmol) in dry tetrahydrofuran (150 ml) in a 250 mL three-necked round-bottomed flask provided with a magnetic stirrer and a dropping funnel. After 24 hours of stirring at room temperature, the 2-dimethylaminoethyl tosylate (50.0 mmol) was added. After 18 hours of stirring the conversion was found to be 96%, and water (100 ml) was carefully added dropwise to the reaction mixture and the tetrahydrofuran was then distilled off. The crude product was extracted with ether and the combined organic phase was then dried with sodium sulphate, and boiled down. The residue was purified on a silica gel column, which resulted in 8.5 g of (dimethylaminoethyl)-di(2-butyl)cyclopentadiene.

b. Synthesis of 1-(dimethylaminoethyl)-2,4-di(2-butyl)-cyclopentadienyltitanium(III) dichloride and [1-dimethylaminoethyl)-2,4-i(2-butyl)cyclopentadienyl] dimethyltitanium(III)

[C$_5$H$_2$(2-C$_4$H$_9$)$_2$(CH$_2$)$_2$NMe$_2$Ti(III)Cl$_2$] and
[C$_5$H$_2$(2-C$_4$H$_9$)$_2$(CH$_2$)$_2$NMe$_2$Ti(III)Me$_2$]

In a Schlenk vessel, 2.36 g (9.48 mmol) of (dimethylaminoethyl)di(2-butyl)cyclopentadiene was dissolved in 50 mL of diethyl ether and the solution then cooled to −60° C. Then 5.9 mL of n-butyllithium (1.6 M in hexane; 9.44 mmol) were added dropwise. The reaction mixture was slowly brought to room temperature, followed by stirring for two hours.

In a second Schlenk vessel, 50 mL of tetrahydrofuran were added to 3.51 g of Ti(III)Cl$_3$.3THF (9.44 mmol).

Both Schlenk vessels were cooled to −60° C. and the organolithium compound was then added to the Ti(III)Cl₃ suspension. The reaction mixture was then stirred for 18 hours at room temperature, after which the solvent was evaporated. To the residue, 50 mL of petroleum ether were added, which was subsequently evaporated to dryness. 2.15 g of a green solid remained containing 1-(dimethylaminoethyl)-2,4-di(2-butyl)cyclopentadienyltitanium(III) dichloride.

In a Schlenk vessel, 0.45 g (1.22 mmol) of 1-dimethylaminoethyl)di(2-butyl)cyclopentadienyltitanium(III) dichloride was dissolved in 40 mL of diethyl ether. The solution was cooled to −60° C. and 1.33 mL of methyllithium (1.84 M in diethyl ether; 2.44 mmol) were then added dropwise. The reaction mixture was slowly brought to room temperature, followed by stirring for one hour. Then the solvent was evaporated. The residue was extracted with 50 mL of petroleum ether, and the filtrate was boiled down. There remained 0.36 g of a black/brown oil containing [1-(dimethylaminoethyl)-2,4-di(2-butyl)cyclopentadienyl]-dimethyltitanium(III).

EXAMPLE XXIII a. Preparation of (dimethylaminoethyl)tri(2-butyl)cyclopentadiene The reaction was carried out in a manner analogous to that for (dimethylaminoethyl)tri(2-propyl)cyclopentadiene. The conversion was 92%. The product was obtained by distillation, with a yield of 64%.

b. Synthesis of 11-(dimethylaminoethyl)-2,3,5-tri(2-butyl)cyclopentadienyltitanium(III) dichloride and [1-(dimethylaminoethyl)-2,3,5-tri(2-butyl)cyclopentadienyl]-dimethyltitanium(III)

[C₅H(2-C₄H₉)₃(CH₂)₂NMe₂Ti(III)Cl₂] and
[C₅H(2-C₄H₉)₃(CH₂)₂NMe2Ti(III)Me₂]

In a 500 mL 3-necked flask, 200 mL of petroleum ether were added to 6.28 g (20.6 mmol) of potassium 1-(dimethylamino-ethyl)-2,3,5-tri(2-butyl)cyclopentadienyl. In a second (1 L) 3-necked flask, 300 mL of tetrahydrofuran were added to 7.65 g (20.6 mmol) of Ti(III)Cl₃.3THF. Both flasks were cooled to −60° C. and the organopotassium compound was then added to the Ti(III)Cl₃ suspension. The reaction mixture containing 1-(dimethylaminoethyl)-2,3,5-tri(2-butyl)cyclopentadienyltitanium(III) dichloride was slowly brought to room temperature, after which stirring was continued for a further 18 hours. This was followed by cooling to −60° C. and 22.3 mL of methyllithium (1.827 M in diethyl ether; 40.7 mmol) were then added. After two hours of stirring at room temperature, the solvent was removed and the residue was dried in vacuo for 18 hours. To the product, 700 mL of petroleum ether were then added, followed by filtration. The filtrate was boiled down and dried in vacuo for two days. There remained 7.93 g of a brown/black oil containing [1-(dimethylaminoethyl)-2,3,5-tri(2-butyl)cyclopentadienyl]-dimethyltitanium(III).

EXAMPLE XXIV

Preparation of (dimethylaminoethyl)di(3-pentyl)cyclopentadiene

The reaction was carried out in a manner analogous to that for (dimethylaminoethyl)di(2-propyl)cyclopentadiene. The conversion was 99%. After preparative column purification on silica gel using, successively, petroleum ether (40–60° C.) and tetrahydrofuran, the yield of (dimethylaminoethyl)di(3-pentyl)-cyclopentadiene was 85%.

EXAMPLE XXV

Preparation of (di-n-butylaminoethyl)di(3-pentyl)cyclopentadiene

The reaction was carried out in a manner analogous to that for (di-n-butylaminoethyl)di(2-pentyl)cyclopentadiene. The conversion was 95%. The product was obtained after preparative column purification on silica gel using, successively, petroleum ether (40–60° C.) and tetrahydrofuran, the yield being 75%.

EXAMPLE XXVI

Preparation of (2-dimethylaminoethyl)-tri-(3-pentyl)cyclopentadiene

The reaction was carried out in a manner analogous to that for (dimethylaminoethyl)tri(2-propyl)cyclopentadiene. The conversion was 94%. After preparative column purification on silica gel using, successively, petroleum ether (40–60° C.) and tetrahydrofuran, the yield of (2-dimethylaminoethyl)-tri-(3-pentyl)cyclopentadiene was 61%.

EXAMPLE XXVII a. Preparation of cyclohexyl(dimethylaminoethyl)di(2-propyl)-cyclopentadiene In a Schlenk vessel at room temperature, a solution of n-butyl-lithium in hexane (25.0 mL; 1.6 mol/L; 40.0 mmol) was added dropwise to a solution of cyclohexyldiisopropyl-cyclopentadiene (9.28 g; 40.0 mmol) in dry tetrahydrofuran (150 mL). Then, in another Schlenk vessel, a solution of n-butyl-lithium in hexane (25.0 mL; 1.6 mol/L; 40.0 mmol) was added dropwise to a cold (−78° C.) solution of dimethyl-aminoethanol (3.56 g; 40.0 mmol) in tetrahydrofuran (100 mL). After an hour and a half's stirring at room temperature, the mixture was again cooled to −78° C. and the solid 2-dimethylaminoethyl tosylate (8.10 g; 40.0 mmol) was added slowly.

The mixture was brought to 0° C., being stirred for 5 minutes in the process, again cooled to −78° C., and then the mixture from the first Schlenk vessel was added all at once. After 16 hours of stirring at room temperature the conversion was 100%. After column chromatography, 1 1.1 g of cyclohexyl(dimethylamino-ethyl)di(2-propyl)cyclopentadiene were obtained.

b. Synthesis of 1-(dimethylaminoethyl)4-cyclohexyl-2,5-di (2-propyl)cyclopentadienyltitanium(III) dichloride and [1-(dimethylaminoethyl)-4-clohexyl-2,5-di(2-propyl)cyclopentadienyl]-dimethyltitanium(III)

[C₅H (c-Hex)(2-C₃H₇)₂(CH₂)₂NMe₂Ti(III)Cl₂] and
[C₅H (c-Hex)(2-C₃H₇)₂(CH₂)₂NMe₂Ti(III)Me₂]

To lithium (dimethylaminoethyl)cyclohexyldi(2-propyl)cyclopentadiene (2.18 g, 7.20 mmol) dissolved in 20 mL of tetrahydrofuran, a cooled slurry (−70° C.) of Ti(III)Cl₃.3THF (2.67 g, 7.20 mmol) in 20 mL of tetrahydrofuran was added at −70° C. The dark-green solution formed was stirred for 72 hours at room temperature. After this had been boiled down, 30 mL of petroleum ether (40–60) were added. After evaporating to dryness once more, a green powder (2.37 g) was obtained containing 1-(dimethyl-aminoethyl) 4-cyclohexyl-2,5-di(2-propyl)cyclopentadienyltitanium (III) dichloride[lithium chloride]. To a slurry of 0.63 g (1.36 mmol) of the [1-(di methylaminoethyl)4-cyclohexyl-2,5di (2-propyl)-cyclopentadienyl-titanium(III) dichloride]•[lithium chloride] obtained above in 30 mL of diethyl ether and cooled to −70° C., 1.70 mL of methyllithium (1.6 M in diethyl ether, 2.72 mmol) was added dropwise. The green-brown slurry immediately darkened. Then the mixture was stirred for one hour at room temperature, boiled down to dryness and dissolved in 40 mL of petroleum ether. After filtration and complete evaporation of the solvent, a black powder (0.47 g, 1.22 mmol) was obtained containing 1-(dimethylaminoethyl)4-cyclohexyl-2,5-di(2-propyl)cyclopentadienyltitanium(III) dimethyl.

EXAMPLE XXVIII
Preparation of (di-n-butylaminoethyl)di(2-propyl) cyclopentadiene The reaction was carried out in a manner analogous to that for (dimethylaminoethyl)di(2-propyl)cyclopentadiene, the tosylate of N,N-di-n-butylaminoethanol being prepared in situ. The conversion was 94%. The non-geminal di-n-butylaminoethyldi(2-propyl)-cyclopentadiene was obtained by distillation with a yield of 53%.

EXAMPLE XXIX
Preparation of (dimethylaminoethyl)-tri-(2-pentyl) cyclopentadiene The reaction was carried out in a manner analogous to that for (dimethylaminoethyl)tri(2-propyl)cyclopentadiene. The conversion was 90%. After preparative column purification on silica gel using, successively, petroleum ether (40–60° C.) and tetrahydrofuran, the yield of (dimethylaminoethyl)-tri-(2-pentyl)cyclopentadiene was 57%.

EXAMPLE XXX
a. Preparation of bis(dimethylaminoethyl) triisopropylcyclopentadiene In a dry 500 mL three-necked flask with a magnetic stirrer, a solution of 62.5 mL of n-butyllithium (1.6 M in n-hexane; 100 mmol) was added under a dry nitrogen atmosphere to a solution of 19.2 g (100 mmol) of triisopropylcyclopentadiene in 250 mL of tetrahydrofuran at −60° C. After heating to room temperature in approximately one hour, stirring continued for a further two hours. After cooling to −60° C., a solution of 2-dimethylaminoethyl tosylate (105 mmol) prepared in situ was added over a period of 5 minutes. The reaction mixture was heated to room temperature, followed by overnight stirring. After addition of water, the product was extracted with petroleum ether (40–60° C.). The combined organic layer was dried with sodium sulphate, and evaporated to dryness under reduced pressure. The conversion was greater than 95%. A portion of the product thus obtained (10.1 g; 38.2 mmol) was again alkylated under the same conditions with 2-dimethylaminoethyl tosylate (39.0 mmol). The bis(2-dimethylaminoethyl)triisopropyl-cyclopentadiene was obtained with a yield of 35% via column chromatography.

b. Synthesis of [1,3-bis(dimethylaminoethyl)-2,4,5-tri(2-propyl)cyclopentadienyltitanium(III) dichloride and [1,3-bis(dimethylaminoethyl)-2,4,5-tri(2-propyl)cyclopentadienyl]-dimethyltitanium(III)

[C$_5$(2-C$_3$H$_7$)$_3$((CH$_2$)$_2$NMe$_2$)$_2$Ti(III)Cl$_2$] and
[C$_5$(2-C$_3$H$_7$)$_3$((CH$_2$)$_2$NMe$_2$)$_2$Ti(III)Me$_2$]

In a 500 mL 3-necked flask, 200 mL of petroleum ether were added to 3.38 g (10.1 mmol) of potassium 1,3-bis(dimethyl-aminoethyl)-2,4,5-tri(2-propyl)cyclopentadienyl. In a second (1 L) 3-necked flask, 300 mL of tetrahydrofuran were added to 3.75 g (10.1 mmol) of Ti(III)Cl$_3$.3THF. Both flasks were cooled to −60° C. and the organopotassium compound was then added to the Ti(III)Cl$_3$ suspension. The reaction mixture containing 1-(dimethylaminoethyl)-2,3,5-tri(2-propyl)cyclopentadienyltitanium(III) dichloride was slowly brought to room temperature, after which stirring was continued for a further 18 hours. This was followed by cooling to −60° C., and 11.0 mL of methyllithium (1.827 M in diethyl ether; 20.1 mmol) were then added. After two hours of stirring at room temperature, the solvent was removed and the residue was dried in vacuo for 18 hours. To the product, 700 mL of petroleum ether were then added, followed by filtration. The filtrate was boiled down and dried in vacuo for two days. There remained 3.62 g of a brown/black oil containing [1,3-bis(dimethylaminoethyl)-2,4,5-tri (2-propyl)cyclopentadienyl]dimethyltitanium(III).

EXAMPLE XXXI
a. Preparation of (dimethylaminoethyl) tricyclohexylcyclopentadiene The reaction was carried out in a manner analogous to that for (dimethylaminoethyl)dicyclohexylcyclopentadiene. The conversion was 91%. The product was obtained via preparative column purification on silica gel using, successively, petroleum ether (40–60° C.) and tetrahydrofuran as the eluent, the yield being 80%.

b. Synthesis of 1-(dimethylaminoethyl)-2,3,5-tricyclohexylcyclopentadienyltitanium(III) dichloride and [1-(dimethylaminoethyl)-2,3,5-tricyclohexylcyclopentadienyl]di-methyltitanium(III)

[C$_5$H(c-Hex)$_3$(CH$_2$)$_2$NMe$_2$Ti(III)Cl$_2$] and
[C$_5$H(c-Hex)$_3$(CH$_2$)$_2$NMe$_2$Ti(III)Me$_2$]

To lithium (dimethylaminoethyl) tricyclohexylcyclopentadiene (2.11 g, 5.70 mmol) dissolved in 20 mL of tetrahydrofuran, a cooled slurry of Ti(III) Cl$_3$.3THF (2.11 g, 5.70 mmol) in 20 mL of tetrahydrofuran was added at −70° C. The dark-green solution formed was stirred for 72 hours at room temperature. After this had been boiled down, 30 mL of petroleum ether (40–60° C.) were added. After evaporating to dryness once more, a mint-green powder (2.80 g) was obtained, containing 1-(dimethylaminoethyl)-2,3,5-tricyclohexylcyclopentadienyltitanium(III) dichloride. To a slurry of 0.50 g (0.922 mmol) of the [1-(dimethylaminoethyl)-2,3,5-tricyclohexylcyclopentadienyl-titanium(III) dichloride]•[lithium chloride] obtained above in 30 mL of diethyl ether and cooled to −70° C., 1.15 mL of methyllithium (1.6 M in diethyl ether, 1.84 mmol) was added dropwise. The green-brown slurry immediately darkened. Then the mixture was stirred for one hour at room temperature, boiled down to dryness and dissolved in 40 mL of petroleum ether. After filtration and complete evaporation of the solvent, a black powder (0.40 g, 0.87 mmol) was obtained containing 1-dimethylaminoethyl)-tricyclohexylcyclopentadienyl-Ti(III)dimethyl.

EXAMPLE XXXII
a. Preparation of (di-n-butylaminoethyl)-tri-(2-pentyl)-cyclopentadiene The reaction was carried out in a manner analogous to that for (di-n-butylaminoethyl)di(3-pentyl)cyclopentadiene. The conversion was 88%. The (2-di-n-butylaminoethyl)di(2-pentyl)cyclopentadiene was obtained after preparative column purification on silica gel using, successively, petroleum ether (40–60° C.) and tetrahydrofuran, followed by distillation under reduced pressure, the yield being 51%.

b. Synthesis of 1-(di-n-butylaminoethyl)-2,3,5-tri(2-pentyl)-cyclopentadienyltitanium(III) dichloride

[C$_5$H(2-C$_5$H$_{11}$)$_3$(CH$_2$)$_2$N(n-BU)$_2$Ti(III)Cl$_2$]

2.633 g (6.11 mmol) of (di-n-butylaminoethyl)tri-(2-pentyl)cyclopentadiene were dissolved in 50 mL of diethyl ether and cooled to −78° C. Then 3.8 mL of n-butyllithium (1.6 M in hexane; 6.11 mmol) were added. After stirring for 18 hours at room temperature, the clear pale-yellow solution was boiled down followed by washing once with 25 mL of petroleum ether. The solvent was then completely evaporated, leaving behind 1.58 g of a yellow oil containing lithium 1-(di-n-butylaminoethyl)-2,3,5-tri(2-pentyl) cyclopentadienyl. Then the organolithium compound was dissolved in 50 mL of tetrahydrofuran and added, at −78° C., to 9.23 g (24.9 mmol) of Ti(III)Cl$_3$.3THF in 50 mL of tetrahydrofuran. After 18 hours of stirring at room temperature, a dark-green solution had formed. After this solution had been completely boiled down, 1.52 g of a green oil remained containing 1-(di-n-butylaminoethyl)-2,3,5-tri (2-pentyl)cyclopentadienyl-titanium(III) dichloride.

EXAMPLE XXXIII a. Preparation of (dimethylaminoethyl) tetraethylcyclopentadiene In a Schlenk vessel, a solution of n-butyllithium in hexane (6.00 mL; 1.65 mol/L; 9.90 mmol) was added dropwise to a solution of tetraethylcyclopentadiene (2.066 g; 11.6 mmol) in dry tetrahydrofuran (20 mL) at room temperature.

Then, in a second Schlenk vessel, a solution of n-butyllithium in hexane (5.90 mL; 1.65 mol/L; 9.74 mmol) was added dropwise to a solution of 2-dimethylaminoethanol (0.867 g; 9.74 mmol) in tetrahydrofuran (35 mL) at −78° C. After two hours of stirring at room temperature, the mixture was again cooled to −78° C. and the solid 2-dimethylaminoethyl tosylate (1.855 g; 9.74 mmol) was added slowly. The mixture was brought to 0° C., being stirred for 5 minutes in the process, and the mixture from the first Schlenk vessel was then added all at once. After 16 hours, the conversion was 100%. After column chromato-graphy, 2.6 g of (dimethylaminoethyl) tetraethylcyclopentadiene were obtained.

b. Synthesis of 1-(dimethylaminoethyl)-2,3,4,5-tetraethylcyclopentadienyltitanium(III) dichloride and [1-(dimethylaminoethyl)-2,3,4,5-tetraethylcyclopentadienyl] dimethyl-titanium(III)

In a Schlenk vessel, 0.38 g of (dimethylaminoethyl) tetraethylcyclopentadiene (1.523 mmol) was dissolved in 20 mL of diethyl ether and the solution was then cooled to −60° C. Then 0.95 mL of n-butyllithium (1.6 M in hexane; 1.52 mmol) were added dropwise. Cooling was stopped after 30 minutes, followed by one hour of stirring at room temperature.

In a second Schlenk vessel, 30 mL of tetrahydrofuran were added to 0.57 g (1.538 mmol) of Ti(III)Cl$_3$.3THF.

Both Schlenk vessels were cooled to −60° C. and the organolithium compound was then added to the Ti(III)Cl$_3$ suspension. The reaction mixture was then stirred for 18 hours at room temperature, after which the solvent was evaporated. To the residue, 50 mL of petroleum ether were added, which was subsequently evaporated to dryness. The residue was a green solid containing 1-(dimethylaminoethyl)-2,3,4,5-tetraethyl-cyclopentadienyltitanium(III) dichloride.

Twenty mL of diethyl ether were added to 0.25 g (0.68 mmol) of the product. After cooling to −60° C., 0.85 mL of methyllithium (1.6 M in diethyl ether; 1.36 mmol) was added, followed by three hours of stirring at room temperature. Then the solvent was removed under reduced pressure. After addition of petroleum ether, filtration and boiling down, 0.17 g of a dark oil was obtained containing 1-[(dimethyl-aminoethyl)-2,3,4,5-tetraethylcyclopentadienyl]dimethyl-titanium(III).

EXAMPLE XXXIV a. Preparation of (dimethylaminoethyl)tetra-n-octylcyclopentadiene In a Schlenk vessel, a solution of n-butyllithium in hexane (24.8 mL; 1.6 mol/L; 39.6 mmol) was added dropwise to a solution of tetra-n-octylcyclopentadiene (20.4 g; 39.6 mmol) in dry tetrahydrofuran (100 mL) at room temperature.

Then, in a second Schlenk vessel, a solution of n-butyllithium in hexane (24.6 mL; 1.6 mol/L; 39.6 mmol) was added dropwise to a solution of 2-dimethylaminoethanol (3.53 g; 39.6 mmol) in tetrahydrofuran (30 mL) at −78° C. After two hours of stirring at room temperature, the mixture was again cooled to −78° C. and the solid 2-dimethylaminoethyl tosylate (7.54 g; 39.6 mmol) was added slowly.

The mixture was brought to 0° C., being stirred for 5 minutes in the process, and the mixture from the first Schlenk vessel was then added all at once. After 16 hours, the conversion was 87%. After column chromatography, 19.2 g of (dimethylaminoethyl)tetra-n-octyl-cyclopentadiene were obtained.

EXAMPLE XXXV a. Preparation of (dimethylaminoethyl)tetra-n-propylcyclopentadiene In a 500 mL 3-neck flask, a solution of n-butyllithium in hexane (93.8 mL; 1.6 mol/L; 150 mmol) was added dropwise to a solution of tetra-n-propylcyclopentadiene (35.0 g; 150 mmol) in dry tetrahydrofuran (200 mL) at room temperature.

Then, in a second Schlenk vessel, a solution of n-butyllithium in hexane (93.8 mL; 1.6 mol/L; 150 mmol) was added dropwise to a solution of 2-dimethylaminoethanol (13.35 g; 150 mmol) in tetrahydrofuran (100 mL) at −78° C. After two hours of stirring at room temperature, the mixture was again cooled to −78° C. and the solid 2-dimethylaminoethyl tosylate (28.5 g; 150 mmol) was added slowly. The mixture was brought to −20° C., being stirred for 5 minutes in the process, and the mixture from the first Schlenk vessel was then added. After 16 hours, the conversion was 97%. After column chromatography, 39.6 g of (dimethylaminoethyl)tetra-n-propylcyclopentadiene were obtained.

b. Synthesis of 1-(dimethylaminoethyl)-2,3,4,5-tetra-n-propyl-cyclopentadienyltitanium(III) dichloride and [1-(dimethylaminoethyl)-2,3,4,5-tetra-n-propylcyclopentadienyl]dimethyltitanium(III)

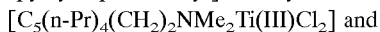
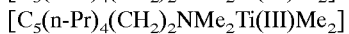

In a Schlenk vessel, 0.62 g of (dimethylaminoethyl)tetra (n-propyl)cyclopentadiene (2.03 mmol) was dissolved in 20 mL of diethyl ether and the solution was then cooled to −60° C. Then 1.27 mL of n-butyllithium (1.6 M in hexane; 2.03 mmol) were added dropwise. Cooling was stopped after 30 minutes, followed by one hour of stirring at room temperature.

In a second Schlenk vessel, 30 mL of tetrahydrofuran were added to 0.75 g (2.03 mmol) of Ti(III)Cl$_3$.3THF.

Both Schlenk vessels were cooled to −60° C., and the organolithium compound was then added to the Ti(III)Cl$_3$ suspension. The reaction mixture was then stirred for 18 hours at room temperature, after which the solvent was evaporated. To the residue, 50 mL of petroleum ether were added, which was subsequently evaporated to dryness. The residue was a green oil containing 1-(dimethylaminoethyl)-2,3,4,5-tetra-n-propylcyclopentadienyl-titanium(III) dichloride. Twenty mL of diethyl ether were added to 0.51 g (1.01 mmol) of the product. After cooling to −60° C., 1.26 mL of methyllithium (1.6 M in diethyl ether; 2.02 mmol) was added, followed by three hours of stirring at room temperature. Then the solvent was removed under reduced pressure. After addition of petroleum ether, filtration and boiling down, 0.31 g of a dark oil was obtained containing 1-[(dimethylaminoethyl)-2,3,4,5-tetra-n-propylcyclopentadienyl]dimethyltitanium(III).

EXAMPLE XXXVI
Preparation of (dimethylaminoethyl)di(2-phenyl-propyl)cyclopentadiene 12.5 mL of a 1.6 molar solution of n-butyllithium in hexane was added dropwise to a cooled (0° C.) solution of di-(2-phenyl-propyl)-cyclopentadiene (6.05 g; 20.0 mmol) in dry tetrahydrofuran (100 ml) under a nitrogen atmosphere in a 250 mL three-necked round-bottomed flask provided with a magnetic stirrer and a dropping funnel. After 24 hours of stirring at room temperature, a solution of 2-dimethylaminoethyl tosylate (20.0 mmol) prepared in situ in tetrahydrofuran/hexane was added. After 18 hours of stirring, the conversion was found to be 90%, and water (100 ml) was carefully added dropwise to the reaction mixture and the tetrahydrofuran was then distilled off. The crude product was extracted with ether, and the combined organic phase was then dried with sodium sulphate, and boiled down. The residue was purified on a silica gel column, which resulted in 5.98 grams (80%) of (dimethyl-aminoethyl)di(2-phenyl-propyl)cyclopentadiene.

EXAMPLE XXXVII
Preparation of [(dimethylaminoethyl)di(2-phenyl-propyl)-cyclopentadienyl]titanium dichloride To (dimethylaminoethyl)di(2-phenyl-propyl)cyclopentadiene (1.12 gram, 3 mmol) dissolved in 20 mL of tetrahydrofuran, 1.87 mL of a 1.6 molar butyllithium-in-hexane solution were added at 0° C. (ice bath). After 15 minutes of stirring, this mixture was cooled further to −78° C., and a slurry of Ti(III)Cl$_3$.3THF (1.11 g, 3 mmol) in 20 mL of tetrahydrofuran, likewise cooled to −78° C., was added. The cooling bath was removed, and the dark-green solution formed was stirred for 72 hours at room temperature. After this had been boiled down, 30 mL of petroleum ether (40–60) were added. After evaporation to dryness once more, a green powder (1.19 g) was obtained containing [(dimethylaminoethyl)di(2-phenyl-propyl)cyclopentadienyl]titanium dichloride.

EXAMPLE XXXVIII
a. Preparation of (dimethylaminoethyl)di(1,1-dimethyl-propyl)cyclopentadiene Twenty-five mL of a 1.6 molar solution of n-butyllithium in hexane was added dropwise to a cooled (0° C. ) solution of di-(1,1-dimethyl-propyl)cyclopentadiene (8.25 g; 40.0 mmol) in dry tetrahydrofuran (125 ml) under a nitrogen atmosphere in a 250 mL three-necked round-bottomed flask provided with a magnetic stirrer and a dropping funnel. After 24 hours of stirring at room temperature, a solution of 2-dimethylaminoethyl tosylate (40.0 mmol) prepared in situ in tetrahydrofuran/hexane was added. After 18 hours of stirring, the conversion was found to be 91%, and water (100 mL) was carefully added dropwise to the reaction mixture and the tetrahydrofuran was then distilled off. The crude product was extracted with ether, and the combined organic phase was then dried with sodium sulphate, and boiled down. The residue was purified on a silica gel column, which resulted in 9.1 grams (82%) of (dimethyl-aminoethyl)di(1,1-dimethyl-propyl)cyclopentadiene.

b. Synthesis of [(dimethylaminoethyl)di(1,1-dimethyl-propyl)-cyclopentadienyl]titanium dichloride To (dimethylaminoethyl)di(1,1-dimethyl-propyl)cyclopentadiene (1.39 gram, 5 mmol) dissolved in 20 mL of tetrahydrofuran, 3.1 mL of a 1.6 molar butyllithium-in-hexane solution were added at 0° C. (ice bath). After 15 minutes of stirring, this mixture was cooled further to −78° C., and a slurry of Ti(III)Cl$_3$.3THF (1.86 g, 5 mmol) in 20 mL of tetrahydrofuran, likewise cooled to −78° C., was added. The cooling bath was removed, and the dark-green solution formed was stirred for 72 hours at room temperature. After this had been boiled down, 30 mL of petroleum ether (40–60) were added. After evaporation to dryness once more, a green powder (1.68 g) was obtained containing [(dimethylaminoethyl)di(1,1-dimethyl-propyl)cyclopentadienyl]titanium dichloride.

EXAMPLE XXXIX
a. Preparation of (dimethylaminomethyl)di(1-methyl-1-ethylpropyl)cyclopentadiene The preparation was carried out as in Example XXXVII, but now using 7.03 grams of di(1-methyl-1-ethyl-propyl)cyclopentadiene (30 mmol), 30 mol of 2-dimethylaminoethyl tosylate and 18.7 mL of 1.6 M butyl-lithium solution. The substituted cyclopentadienes was 90% (dimethylaminomethyl)di(1-methyl-1-ethyl-propyl)cyclopentadiene and, after purification on the column, 79% (7.24 grams) were obtained.

b. Synthesis of [(dimethylaminoethyl)di(1-methyl-1-ethyl-propyl)-cyclopentadienyl]titanium dichloride The synthesis was carried out as in Example XXXVIII, but now using: 1.53 grams of (dimethylaminomethyl)di(1-methyl-1-ethyl-propyl)cyclopentadiene. 1.76 grams of [(dimethylaminoethyl)di(1-methyl-1-ethyl-propyl)cyclopentadienyl]titanium dichloride were obtained.

EXAMPLE XXXX
Preparation of ligands from alkenyllithium compounds and esters Preparation of (N N-di-n-decylaminoethyl)tetramethylcyclopentadiene In a three-necked flask, 1.5 g (216 mmol) of Li wire were added to 200 mL of diethyl ether. The solution was cooled to 0° C., followed by slow dropwise addition of 10.0 mL (98 mmol) of 2-bromo-2-butene. Stirring continued at room temperature for 30 minutes. The solution became green/yellow in colour. Then the solution was cooled to −25° C. and 13.05 grams (33.89 mmol) of N,N-di-n-decyl-aminoethyl propionate were slowly added dropwise with cooling. The temperature rose to 0° C. The reaction mixture was then stirred for a further 5 minutes at room temperature, followed by slow dropwise addition of 20 mL of water. The water and ether layers were separated, and the water layer was extracted with 2×50 mL of diethyl ether. The collected ether layer was dried with magnesium sulphate, filtered and boiled down. The residue was a pale-yellow liquid containing 4-(N,N-di-n-decylaminoethyl)4-hydroxy-hepta-2,5-diene, which was characterized via NMR. The yield was 15.0 grams. In a three-necked flask, 10.0 grams of p-toluenesulphonic acid monohydrate (52.6 mmol) were dissolved in 150 mL of diethyl ether. To this, 15.0 g of the obtained carbinol (32.49 mmol) were added dropwise. During the dropwise addition, a white suspension was formed. This was followed by two hours of stirring at room temperature. The solution was neutralized with Na$_2$CO$_3$ solution. The water and ether layers were separated, and the water layer was extracted with 2×50 mL of diethyl ether. The collected ether layers were dried, and the drying agent was filtered off. Then the diethyl ether was evaporated. The residue contained carbinol (30%) and ligand (70%). Yield: 11 grams of crude product (76%). Five grams of this crude mixture were purified by column chromatography to give 3 g of pure ligand. According to this method, the following ligands were synthesized (Cp'=Me$_4$C$_5$; Et=(CH$_2$)$_2$):

| | |
|---|---|
| Cp'EtN(ethyl)$_2$ | Yield (30%) |
| (Et$_2$)(Me$_2$)C$_5$(CH$_2$)$_2$NMe$_2$ | Yield (15%) |
| Cp'EtN(iButyl)$_2$ | Yield (20%) |
| Cp'CH(CH$_3$)CH$_2$N(ethyl)$_2$ | Yield (30%) |
| Cp'EtN(Me)Pr | Yield (15%) |
| Cp'EtN(n-Bu)$_2$ | Yield (50%) |
| Cp'EtN(cyclohexyl)$_2$ | Yield (30%) |
| Cp'EtN(secButyl)$_2$ | Yield (15%) |
| Cp'EtN(ethyl)(phenyl) | Yield (10%) |
| Cp'EtN(ipropyl)(cyclohexyl) | Yield (15%) |
| Cp'EtN(Me)(ethylphenyl) | Yield (25%) |
| Cp'EtN(2-methoxyethyl)$_2$ | Yield (25%) |

EXAMPLE XXXXI a. Preparation of (N, N',N'-trimethyl-3,6-diazaheptyl)tetramethylcyclopentadiene From 2-lithium-2-butene and EtQC(O)CH$_2$CH$_2$N(Me)CH$_2$-CH$_2$NMe$_2$, the compound specified in the opening lines was prepared by the method described in DE-A4303647, with a yield of 25% based on the amount of ester used as a starting material.

b. Synthesis of [1-(N,N',N'-trimethyl-3,6-diazaheptyl)-2,3,4,5-tetramethylcyclopentadienyl]dichlorotitanium (III)

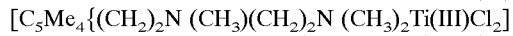

In a Schlenk vessel, 0.21 g (0.838 mmol) of (N,N',N'-trimethyl-3,6-diazaheptyl)tetramethylcyclopentadiene was dissolved in 15 mL of tetrahydrofuran and the solution was then cooled to –60° C. Then 0.52 mL of n-butyllithium (1.6 M in hexane; 0.832 mmol) were added dropwise. Cooling was stopped after 2.5 hours, followed by minutes of stirring at room temperature.

In a second Schlenk vessel, 15 mL of tetrahydrofuran were added to 0.31 g (0.836 mmol) of Ti(III)Cl$_3$.3THF.

Both Schlenk vessels were cooled to –60° C. and the organolithium compound was then added to the Ti(III)Cl$_3$ suspension. Cooling was stopped after two hours, followed by a further two hours of stirring at room temperature. Then the solvent was evaporated. To the residue containing [1-(N,N',N'-trimethyl-3,6-diazaheptyl)-2,3,4,5-tetramethylcyclopentadienyl]titanium(III) dichloride, 40 mL of petroleum ether were added which were subsequently evaporated again. The synthesized catalyst was not worked up further.

EXAMPLE XXXXII a. Preparation of 1-(N-methyl-N-(dioxolylmethyl)ethyl)2,3,4,5-tetramethylcyclopentadienyltitanium(III) dichloride

To 0.36 g (1.33 mmol) of lithium 1-(N-methyl-N-(dioxolyl-methyl)ethyl)-2,3,4,5-tetramethylcyclopentadienyl, 40 mL of petroleum ether were added in a Schlenk vessel.

To 0.50 g of Ti(III)Cl3.3THF (1.35 mmol), 30 mL of tetrahydrofuran were added in a second Schlenk vessel.

Both Schlenk vessels were cooled to –60° C., and the organolithium compound was then added to the Ti(III)Cl$_3$ suspension. The reaction mixture was stirred at room temperature for 18 hours and the solvent was then evaporated. Fifty mL of petroleum ether were added to the residue, followed by evaporation once more. The residue was a green solid containing 1-[(N-methyl-N-(dioxolyl-methyl)ethyl]-2,3,4,5-tetramethylcyclopentadienyltitanium(III) dichloride.

EXAMPLE XXXXIII a. Preparation of 1,2,3,4-tetramethyl-5(2-chloroethyl)cyclopentadiene A 1-liter three-necked flask, provided with a dropping funnel, condenser, mechanical stirrer and nitrogen inlet, was charged with 30.5 g of 1,2,3,4-tetramethylcyclopentadiene (0.25 mol), dissolved in 700 mL of ethoxyethane, and cooled to 2° C. Then 160 mL of n-butyllithium (1.6 M in hexane; 0.26 mol) were added dropwise in two hours, followed by 18 hours of stirring at room temperature with the aid of a mechanical stirrer. Then 36.0 g of 1-bromo-2-chloroethane (0.25 mol) were added all at once. The reaction mixture was stirred at room temperature for 10 days. GC analysis of a sample showed that the conversion of the tetramethylcyclopentadiene was 91%. One hundred ml of water were added to the reaction mixture, followed by separation of the water phase and the organic phase. The organic layer was washed once with 50 mL of saturated aqueous sodium chloride solution, dried with sodium sulphate, filtered and boiled down. The residue (43.9 g) proved to have the following composition according to gas chromatography (GC) analysis: apart from the starting materials, 1-bromo-2-chloroethane (9 wt %) and 1,2,3,4-tetramethylcyclopentadiene (9 wt %). Only non-geminally coupled product (84%) and geminally coupled product (16%) were found to be present.

b. Preparation of 4,5,6,7-tetramethyl-spiro[2,4-hepta-2,4-diene

The product obtained under a. (43.9 g), which according to GC analysis contains approximately 32 g of 1,2,3,4-tetramethyl-5(2-chloroethyl)cyclopentadiene (0.175 mol), was dissolved in 300 mL of tetrahydrofuran. The solution was cooled to –60° C., followed by dropwise addition of 115 mL of n-butyllithium (1.6 M in hexane; 0.184 mol). The reaction mixture was brought to room temperature, followed by 40 hours of stirring.

The tetrahydrofuran was evaporated and the residue was taken up in 200 mL of ethoxyethane. One hundred mL of water were added, and the water phase and organic phase were then separated. The organic phase was washed once with 100 mL of water. The combined water layer was extracted once with ethoxyethane. The combined organic layer was washed once with 50 mL of saturated sodium chloride solution, dried with sodium sulphate, filtered and boiled down. The residue (43.2 g) was a pale-yellow liquid which was purified with the aid of column chromatography (silica gel, mobile solvent petroleum ether). The yield was 24.2 g of a colourless liquid which was characterized with the aid of $^1$H-NMR and by means of GC-MS as 4,5,6,7-tetramethyl-spiro[2.4]-hepta-2,4-diene. The yield was 93%, based on the amount of 1,2,3,4-tetramethyl-5-(2-chloroethyl)cyclopentadiene used, and 65% based on 1,2,3,4-tetramethylcyclopentadiene.

c. Synthesis of 1,2,3,4-tetramethyl-5(2-P,P-diphenylphosphinoethyl)cyclopentadiene 3.87 g of diphenylphosphine (21 mmol) were dissolved, in a 100 mL reactor, in 25 mL of tetrahydrofuran and cooled to 2° C. Then 13.0 mL of n-butyllithium (1.6 M in hexane, 21 mmol) were added dropwise followed by stirring for half an hour at 2° C. Stirring then continued for one hour at room temperature. The dark-red mixture obtained was then cooled to –60° C. To this, 3.08 g of 4,5,6,7-tetramethyl-spiro[2.4]-hepta-2,4-diene (21 mmol) as obtained under b. were added all at once. The reaction mixture was brought to room temperature and stirred for three days. Then, the tetrahydrofuran was evaporated.

The residue, a yellow solid, was washed twice with petroleum ether at 0° C. The solid was then suspended in 50 mL of ethoxyethane and 5 mL of water were added dropwise. The ether layer and water layer were separated. The water layer was extracted a further three times with 25 mL of ethoxyethane. The combined ether layers were then boiled down, whereupon 4.72 g of a pale-brown, clear viscous liquid were obtained.

$^{31}$P-NMR and $^1$H-NMR analysis showed that the residue was 1,2,3,4-tetramethyl-5(2-P,P-diphenylphosphinoethyl)-cyclopentadiene. The yield of 1,2,3,4-tetramethyl-5(2-P,P-diphenylphosphinoethyl)-cyclopentadiene, based on 4,5,6,7-tetramethyl-spiro[2.4]-hepta-2,4-diene, was 67%. After GC analysis of the product, the purity was found to be >98%.

d. Synthesis of 1,2,3,4tetramethyl-5(2-P,P-dimethylphosphinoethyl)cyclopentadiene Lithium dimethylphosphide was prepared by reaction of dimethylphenylphosphine and lithium, hydrolysis with water, distillation of dimethylphosphine and reaction of the latter with butyllithium (see T.-s. Chou et al., *J. Org. Chem.* 1985, 50, 4329).

In a 250 mL reactor, 8.12 g of lithium-dimethylphosphide solution in tetrahydrofuran (14 mmol) were mixed with 25 mL of tetrahydrofuran. The solution obtained was cooled to −90° C. To this solution, 1.7 g of 4,5,6,7-tetramethyl-spiro [2.4]-hepta-2,4-diene (12 mmol) as obtained under b., was then added all at once. The reaction mixture was brought to room temperature and stirred for two days, followed by dropwise addition of 20 mL of water. Then the tetrahydrofuran was evaporated and the residue was extracted with ether (ethoxyethane). The combined ether layers were boiled down and the residue distilled in vacuo.

The boiling point of the product was 51–52° C. at 0.01 mm Hg. As $^{31}$P-NMR and $^1$H-NMR analysis showed, the distilled product (1.13 g) was mainly 1,2,3,4-tetramethyl-5 (2-P,P-dimethylphosphinoethyl)-cyclopentadiene. The yield of 1,2,3,4-tetramethyl-5(2-P,P-dimethylphosphinoethyl)-cyclopentadiene based on 4,5,6,7-tetra-methyl-spiro[2.4]-hepta-2,4-diene was 46%. After GC analysis, the purity was found to be >95%.

EXAMPLE XXXXIV a. Preparation of (1,2,3,4-tetramethylcyclopentadien-5-yl) chloromethyldimethylsilane.

In a 1500 mL reactor, 31.0 g of tetramethylcyclopentadiene (0.24 mol) were dissolved in 500 mL of tetrahydrofuran and cooled to 2° C. Then 160 mL of n-butyllithium (1.6 M in hexane, 0.26 mol) were added dropwise, followed by stirring at room temperature for 18 hours with a mechanical stirrer. The reaction mixture obtained was cooled to −90° C. Then 36.3 g of chloromethyldimethylsilyl chloride (0.28 mol) were added all at once. Then the cooling bath was removed, and the reaction mixture was allowed to come to room temperature and stirred for 18 hours. Then 200 mL of water were added. The tetrahydrofuran was evaporated in a rotary evaporator, and the residue was extracted three times with 200 mL of ethoxyethane. The combined ether layers were dried with sodium sulphate, the sodium sulphate was filtered off, and the filtrate was boiled down. The residue (58.0 g) had a purity determined by means of gas chromatography (GC) of >98% of (1,2,3,4-tetramethylcyclopentadien-5-yl)-chloromethyldimethylsilane.

b. Synthesis of (diphenylphosphinomethyl) (1,2,3,4-tetramethylcyclopentadien-5-yl)dimethylsilane 15.9 g of diphenylphosphine (85 mmol) were dissolved in 100 mL of ether. The solution was cooled to 2° C., followed by dropwise addition of 53 mL of n-butyllithium (1.6 M in hexane, 85 mmol). After this had been metered in, the mixture was stirred for half an hour at 2° C. and then for 18 hours at room temperature (the lithium-diphenylphosphine was not completely soluble). Then 100 mL of tetrahydrofuran were added, a dark-red homogeneous solution being obtained as a result. This solution was added dropwise to a solution of 19.5 g (85 mmol) of (1,2,3,4-tetramethylcyclopentadien-5-yl)-chloromethyldimethylsilane as obtained under a., in 150 mL of tetrahydrofuran at 2° C. The reaction mixture was stirred for 18 hours at room temperature, and the tetrahydrofuran was then evaporated. Two hundred mL of petroleum ether were added to the residue, the precipitate was filtered off and the filtrate was boiled down. The residue was pure (diphenylphosphinomethyl) (1,2,3,4-tetramethylcyclopentadien-5-yl)dimethylsilane. The yield was 31.8 g.

c. Synthesis of (1,2,3,4-tetramethylcyclopentadien-5-methylyl) (N,N-diisopropylamino)dimethylsilane.

1.22 g of diisopropylamine (12 mmol) was dissolved in 25 mL of tetrahydrofuran and cooled to 2° C. Then 7.5 mL of n-butyllithium (1.6 M in hexane; 12 mmol) were added dropwise, followed by half an hour's stirring at room temperature. To the solution obtained, 2.70 g of (1,2,3,4-tetramethylcyclopentadien-5-yl)chloromethyl-dimethylsilane (12 mmol) as obtained under a. were added dropwise. The reaction mixture was stirred at room temperature for 18 hours. The tetrahydrofuran was evaporated, and 100 mL of ether were added to the residue, after which the salts formed were filtered off and the filtrate was boiled down, 3.0 g of residue being obtained. GC analysis showed a conversion of 100% and a purity of >90% of (1,2,3,4-tetramethylcyclopentadien-5-methylyl) (N,N-diisopropylamino)dimethylsilane.

d. Synthesis of (1,2,3,4-tetramethylcyclopentadien-5-methylyl) (N,N-di-n-butylamino)dimethylsilane.

The synthesis under c. was repeated, the starting materials being 1.75 g (13.5 mmol) of di-n-butylamine and 3.05 g of (1,2,3,4-tetramethylcyclopentadien-5-yl)-chloromethyidimethylsilane (13.3 mmol). GC analysis showed 100% conversion. After boiling down, 3.95 g of (1,2,3,4-tetramethylcyclopentadien-5-methylyl) (N,N-di-n-butylamino)dimethylsilane were obtained.

EXAMPLE XXXXV

Synthesis of 1-(diphenylphosphinoethyl)-2,3,4,5-tetramethylcyclopentadienyltitanium(III) dichloride

[C$_5$Me$_4$(CH$_2$)$_2$PPh$_2$Ti(III)Cl$_2$]

In a Schlenk vessel, 1.14 g (3.408 mmol) of (diphenylphosphinoethyl)tetramethylcyclopentadiene were dissolved in 30 mL of diethyl ether and the solution was then cooled to −60° C. Then 2.13 mL of n-butyllithium (1.6 M in hexane; 3.41 mmol) were added dropwise. The reaction mixture was slowly brought to room temperature, followed by two hours of stirring.

In a second Schlenk vessel, 40 mL of tetrahydrofuran were added to 1.26 g of Ti(III)Cl$_3$.3THF (3.40 mmol).

Both Schlenk vessels were cooled to −60° C. and the organolithium compound was then added to the Ti(III)Cl$_3$ suspension. The reaction mixture was then stirred for 60 hours at room temperature, after which the solvent was evaporated. To the residue, 50 mL of petroleum ether were added, which was subsequently evaporated to dryness. There remained a green solid containing 1-(diphenylphosphinoethyl)-2,3,4,5-tetramethylcyclopentadienyl-titanium(III) dichloride.

EXAMPLE XXXXVI 1-(dimethylphosphinoethyl)-2,3,4,5-tetramethylcyclopentadienyl-titanium(III) dichloride

[C$_5$Me$_4$(CH$_2$)$_2$PMe$_2$Ti(III)Cl$_2$]

In a Schlenk vessel, 0.78 g (3.709 mmol) of (dimethylphosphinoethyl)tetramethylcyclopentadiene was dissolved in 30 mL of diethyl ether and the solution was then cooled to −60° C. Then 2.32 mL of n-butyllithium (1.6M in hexane; 3.71 mmol) were added dropwise. The reaction mixture was slowly brought to room temperature, followed by two hours of stirring. A white suspension was produced.

In a second Schlenk vessel, 40 mL of tetrahydrofuran were added to 1.37 g of Ti(III)Cl$_3$.3THF (3.70 mmol).

Both Schlenk vessels were cooled to −60° C. and the organolithium compound was then added to the Ti(III)Cl$_3$ suspension. The reaction mixture was then stirred for 18 hours at room temperature, after which the solvent was evaporated. To the residue, 50 mL of petroleum ether were added, which was subsequently evaporated to dryness. There remained a green solid containing 1-(dimethylphosphinoethyl)-2,3,4,5-tetramethylcyclopentadienyltitanium(III) dichloride.

EXAMPLE XXXXVII

Synthesis of {1-[(2-diphenylphosphino-1-sila-1-dimethyl)ethyl]-2,3,4,5-tetramethylcyclopentadienyl}titanium(III) dichloride and {1-[(2-diphenylphosphino-1-sila-1,1-dimethyl)ethyl]-2,3,4,5-[tetramethylcyclopentadienyl]}dimethyltitanium(III)

[C$_5$Me$_4$(Si(CH$_3$)$_2$CH$_2$)PPh$_2$Ti(III)Cl$_{12}$] and
[C$_5$Me$_4$(Si(CH$_3$)$_2$CH$_2$)PPh$_2$Ti(III)Me$_2$]

To 1.57 g (4.15 mmol) of [(2-diphenylphosphino-1,1-dimethyl)ethyl]tetramethylcyclopentadiene, dissolved in 10 mL of diethyl ether, 8.3 mL of lithiumdiisopropylamide (0.5 M in diethyl ether; 4.15 mmol) were added at −78° C. After 18 hours of stirring at room temperature, a turbid yellow/orange solution had formed. The diethyl ether was evaporated, and the residue was washed twice with petroleum ether.

After this had been well boiled down, there remained 1.41 g of a pale-yellow crystalline product containing lithium [(2-diphenyl-phosphino-1-sila-1,1-dimethyl)ethyl]tetramethylcyclopentadienyl.

The organolithium compound was dissolved in 20 mL of tetrahydrofuran. Then the yellow/orange solution was added, at −78° C., to 1.36 g (3.76 mmol) of Ti(III)Cl$_3$.3THF. The reaction mixture was then stirred for three hours in the cold bath and afterwards for 18 hours at room temperature. A dark-green solution had now formed, which was boiled down and washed twice with 10 mL of petroleum ether. There now remained 1.5 g of a green solid containing {1-[(2-diphenylphosphino-1-sila-1,1-dimethyl)ethyl]-2,3,4,5-tetramethylcyclopentadienyl}titanium(III) dichloride.

To 0.534 g (1.08 mmol) of {1-[(2-diphenylphosphino-1-sila-1,1-dimethyl)ethyl]-2,3,4,5-tetramethylcyclopentadienyl}titanium(III) dichloride]•[lithium chloride], 20 mL of diethylether were added, followed by the addition of 1.35 mL of methyllithium (1.6 M in hexane; 2.16 mmol) at −70° C. After two hours of stirring at room temperature, the solvent was removed and the residue dried for two hours in vacuo. Twenty mL of petroleum ether were then added to the product, followed by filtration. The filtrate was boiled down, followed by drying for 18 hours in vacuo. There remained 0.42 g of a brown/black oil containing {1-[(2-diphenylphosphino-1-sila-1,1-dimethyl)ethyl]-2,3,4,5-tetramethylcyclopentadienyl}dimethyl-titanium(III).

EXAMPLE XXXXVIII

Synthesis of {1-[(2-dimethylphosphino-1-sila-1,1-dimethyl)ethyl]-2,3,4,5-tetramethylcyclopentadienyl}titanium(III) dichloride

[C$_5$Me$_4$(Si(CH$_3$)$_2$CH$_2$)PMe$_2$Ti(III)Cl$_2$]

To 0.88 g (4.42 mmol) of [(2-dimethylphosphino-1-sila-1,1-dimethyl)ethyl]tetramethylcyclopentadiene, dissolved in 25 mL of diethyl ether, 8.8 mL of lithiumdiisopropylamide (0.5 M in diethyl ether; 4.42 mmol) were added at −78° C. After 18 hours of stirring at room temperature, a clear pale-yellow solution had formed. The diethyl ether was evaporated. After this had been well boiled down, there remained 1.14 g of a yellow oil containing lithium [(2-dimethylphosphino-1-sila-1,1-dimethyl)ethyl]tetramethylcyclopentadienyl.

The organolithium compound was dissolved in 20 mL of tetrahydrofuran. Then the yellow/orange solution was added to 1.36 g (3.76 mmol) of Ti(III)Cl$_3$.3THF at −78° C. The reaction mixture was then stirred for three hours in the cold bath, and afterwards for 18 hours at room temperature. A dark-green solution had now formed, which was boiled down and washed twice with 10 mL of petroleum ether. There now remained 1.5 g of a green solid containing {1-[(2-dimethylphosphino-1-sila-1,1-dimethyl)ethyl]-2,3,4,5-tetramethylcyclopentadienyl}titanium(III) dichloride.

1.13 g (4.41 mmol) of the organolithium compound was dissolved in 30 mL of tetrahydrofuran and cooled to −78° C. This was then added to a cold suspension of 1.67 g (4.5 mmol) of Ti(III)Cl$_3$.3THF in 25 mL of tetrahydrofuran, followed by three hours of stirring at room temperature. The brown/green slurry was boiled down and washed twice with petroleum ether. There remained 730 mg of a dark-green precipitate containing {1-[(2-dimethylphosphino-1-sila-1,1-dimethyl)ethyl]-2,3,4,5-tetramethylcyclopentadienyl}-titanium(III) dichloride.

EXAMPLE XXXXIX

Synthesis of {1-[(2-dibutylamino-2-sila-2,2-dimethyl)ethyl]-2,3,4,5-tetramethylcyclopentadienyl}titanium(III) dichloride

[CMe4(CH$_2$Si(CH$_3$)$_2$N(n-C$_4$H$_9$)$_2$Ti(III)Cl$_2$]

1.39 g (4.33 mmol) of [(2-dibutylamino-2-sila-2,2-dimethyl)ethyl]tetramethylcyclopentadiene was dissolved in 25 mL of diethyl ether, followed by the addition of 9.0 mL of lithium dibutylamide (0.5M in diethyl ether; 4.5 mmol) at −78° C. This reaction mixture was stirred for 18 hours, after which a turbid yellow suspension had formed. The solvent was removed, followed by washing with petroleum ether for a number of times. After boiling down completely there remained a yellow/brown oil containing lithium 1-[(2-dibutylamino-2-sila-2,2-dimethyl)ethyl]-2,3,4,5-tetramethylcyclopentadienyl. 4.33 mmol of the organolithium compound thus obtained were dissolved in 25 mL of tetrahydrofuran and added to 1.95 g (5.26 mmol) of Ti(III)Cl$_3$.3THF in 25 mL of tetrahydrofuran at −70° C. After three hours of stirring at room temperature, the green/brown solution was completely boiled down and washed twice with 10 mL of petroleum ether.

There remained 1.5 g of a red/brown oil containing {1-[(2-dibutylamino-2-sila-2,2-dimethyl)ethyl]-2,3,4,5-tetramethyl-cyclopentadienyl}titanium(III) dichloride.

EXAMPLE L

Synthesis of [[(di-n-butylamino)dimethylsilyl]tetramethyl-cyclopentadienyl titanium dichloride

[(n-Bu)$_2$NSiMe$_2$C$_5$Me$_4$TiCl$_2$]

a. Preparation of [(di-n-butylamino)dimethylsilyl]tetramethyl-cyclopentadiene

A 250 mL roundbottom flask equipped with a condenser, stirrer, thermometer and dropping funnel with nitrogen inlet was charged with 50 mL diethyl ether in which di-n-butylamine (3.8 g, 27 mmol) was dissolved. The solution was cooled to 0° C. and n-butyllithium (26 mmol, 1.6 M in hexane) was added; the solution was stirred for 2 hours at 2° C. and 30 minutes at room temperature. The solution was then cooled to –90° C. and tetramethylcyclopenta-dienyl (dimethylsilylchloride) (5.7 g, 27 mmol) was added in one portion. The mixture was then stirred for 16 hours allowing the temperature of the reaction mixture to rise to room temperature. A precipitate was filtered off and the solvent was evaporated. The remaining residue was distilled at sub-atmospheric pressure (2.7 mbar) at 130° C. to obtain di-n-butylamino-dimethylsilyl-tetramethylcyclopentadiene (3.4 g). The product was characterized by GC, GC-MS, $^{13}$C and $^{1}$H NMR.

b. Preparation of [(di-n-butylamino)dimethylsilyl] tetramethyl-cyclopentadienyl titanium dichloride In a flask N,N-di-n-butylamine (0.42 g, 3.26 mmol) was added to 10 mL THF. The solution was cooled to –60° C. and one equivalent of butyllithium (2.0 mL, 1.6 M in hexane) was added. The cooling bath was removed and the temperature of the reaction mixture was allowed to rise to room temperature in 20 minutes. The solution was then cooled back down to –60° C. Subsequently the ligand from step a above was added (1.0 g, 3.26 mmol) and the solution stirred for 2 hours at room temperature. A cooled (–60° C.) solution of TiCl$_3$.3THF (1.21 g, 3.26 mmol) in 10 mL THF was added and the mixture stirred for 2.5 hours. The solvent was evaporated and the residue washed with ligroin and dried to obtain [(di-n-butylamino)dimethylsilyl]-tetramethylcyclopentadienyl titanium dichloride (1.2 g).

EXAMPLE Ll

Synthesis of [(dimethylphosphino)dimethylsilyl] tetramethyl-cyclopentadiene titanium dichloride (Me$_2$PSiMe$_2$C$_5$Me$_4$)TiCl$_2$ a. Preparation of [(dimethylphosphino)dimethylsilyl] tetramethyl-cyclopentadiene A 250 mL roundbottom flask equipped with a condenser, stirrer, thermometer and dropping funnel with nitrogen inlet was charged with 100 mL of diethyl ether in which tetramethylcyclopentadienyl-dimethylsilylchloride (8.0 g, 37 mmol) was dissolved. The solution was cooled to –100° C. and lithium-dimethylphosphide (11.22 g in 50 mL THF, 18 mmol) was added; the solution was stirred for 16 hours allowing the temperature of the reaction mixture to rise to room temperature. A precipitate was filtered off and washed with diethyl ether. The organic layers were combined and the solvent evaporated. The remaining residue was distilled at sub-atmospheric pressure (2.4 mbar) at 123° C. to obtain [(dimethylphosphino)dimethylsilyl] tetramethylcyclopentadiene (0.9 g). The product was characterized by GC, GC-MS, $^{13}$C and $^{1}$H NMR.

b. Preparation of [(dimethylphosphino)dimethylsilyl] tetramethyl-cyclopentadienyl titanium dichloride In a flask dimethylphosphine (0.2 g, 3.26 mmol) was added to 10 mL THF. The solution was cooled to –60° C. and one equivalent of butyllithium (2.0 mL, 1.6 M in hexane) was added. The cooling bath was removed and the temperature of the reaction mixture was allowed to rise to room temperature in 20 minutes. The solution was then cooled back down to –60° C. Subsequently the ligand from step a above was added (0.77 g, 3.26 mmol) and the solution stirred for 2 hours at room temperature. A cooled (–60° C.) solution of TiCl$_3$.3THF (1.21 g, 3.26 mmol) in 10 mL THF was added and the mixture stirred for 2.5 hours. The solvent was evaporated and the residue dried to obtain [(dimethylphosphino)dimethylsilyl] tetramethylcyclopentadienyl titanium dichloride in quantitative yield.

EXAMPLE Lll

Synthesis of [(N,N-dimethylamino)dimethylsilyl] tetramethyl-cyclopentadiene titanium dichloride (Me$_2$NSiMe$_2$C$_5$Me$_4$)TiCl$_2$ a. Preparation of [(N,N-dimethylamino)dimethylsilyl] tetramethyl-cyclopentadiene A 250 mL roundbottom flask equipped with a condenser, stirrer, thermometer and dropping funnel with nitrogen inlet was charged with 100 mL of dimethylamine solution (2.0 M in THF, 0.20 mol) and cooled to 15° C. A solution of tetramethylcyclopenta-dienyldimethylsilylchloride in THF (10.1 g in 30 mL THF, 47 mmol) was added and the solution stirred for 16 hours allowing the temperature of the reaction mixture to rise to room temperature. A precipitate was filtered off and the solvent evaporated. The remaining residue was distilled at sub-atmospheric pressure (2.6 mbar) at 80–81° C. to obtain [(N,N-dimethylamino)dimethylsilyl] tetramethyl-cyclopentadiene (4.2 g). The product was characterized by GC, GC-MS, $^{13}$C and $^{1}$H NMR.

b. Preparation of [(N,N-dimethylamino)dimethylsilyl] tetramethyl-cyclopentadienyl titanium dichloride In a flask N,N-dimethylamine (0.15 g, 3.26 mmol) was added to 10 mL THF. The solution was cooled to –60° C. and one equivalent of butyllithium (2.0 mL, 1.6 M in hexane) was added. The cooling bath was removed and the temperature of the reaction mixture was allowed to rise to room temperature in 20 minutes. The solution was then cooled back down to –60° C. Subsequently the ligand from step a above was added (0.72 g, 3.26 mmol) and the solution stirred for 2 hours at room temperature. A cooled (–60° C.) solution of TiCl$_3$.3THF (1.21 g, 3.26 mmol) in 10 mL THF was added and the mixture stirred for 2.5 hours. The solvent was evaporated and the residue dried to obtain [(N,N-dimethylamino)dimethylsilyl]tetramethyl-cyclopentadienyl titanium dichloride in quantitative yield.

EXAMPLE Llll

Synthesis of [(di-isopropylphosphino)dimethylsilyl] tetramethyl-cyclopentadienyl titanium dichloride

[(i-Pr)$_2$PSiMe$_2$C$_5$Me$_4$]TiCl$_2$ a. Preparation of [(di-isopropylphosphino)dimethylsilyl] tetramethyl-cyclopentadiene A 500 mL roundbottom flask equipped with a condenser, stirrer, thermometer and dropping funnel with nitrogen inlet was charged with 125 mL of THF in which tetramethylcyclopentadienyl-dimethylchlorosilane (11.0 g) was dissolved. A solution of lithium diisopropylphosphide [(55 mL, 1.6 M in hexane), which was prepared from 10.38g di-isopropylphosphine and butyllithium] was added, with the temperature of the reaction controlled so as to not exceed 30° C. The solution was then stirred for 16 allowing the temperature to rise to room temperature. The solvent was evaporated and 500 mL diethyl ether was added. The LiCl precipitate was removed by filtration after which the diethyl ether was evaporated. The solid residue was twice washed with 50 mL portions of ligroin and then dried to obtain lithium[(di-isopropylphosphino)dimethylsilyl]-tetramethylcyclopentadienyl (6.2g). The product was characterized by $^{1}$H and $^{31}$p NMR.

b. Preparation of [(di-isopropylphosphino)dimethylsilyl] tetramethyl-cyclopentadienyl titanium dichloride A 1000 mL roundbottom flask was charged with TiCl$_3$.3THF (12.4 g, 33.5 mmol) and 150 mL THF. The solution was cooled to −60° C. A solution of lithium[(di-isopropylphosphino)dimethylsilyl]-tetramethylcyclopentadienyl (33mmol) was added and the reaction mixture stirred for 2.5 hours while allowing the temperature of the reaction mixture to rise to room temperature. The solvent was evaporated and the residue was washed with ligroin giving the product, [(di-isopropylphosphino)dimethylsilyl]tetramethyl-cyclopentadienyl titanium dichloride, in quantitative yield.

EXAMPLE LIV

Synthesis of pentamethylbenzyl(N-t-butyl)amino titanium dichloride

a. Preparation of pentamethylbenzyl(N-t-butylamine

A 500 mL roundbottom flask equipped with a condenser, stirrer, thermometer and dropping funnel with nitrogen inlet was charged with 100 mL diethyl ether in which t-butylamine (8.32g, 0.114 mmol) was dissolved. The solution was cooled to −33° C. and one equivalent of butyllithium (72 mL, 1.6 M in hexane) was added in 15 minutes. After the temperature of the reaction mixture was allowed to rise to room temperature, 75 mL THF was added. The temperature rose slightly from 20° C. to 22° C. and held for 15 minutes. NMR analysis showed 90% conversion to the desired product. The reaction mixture was cooled in an ice/water bath and quenched with NH$_4$Cl. The layers were separated and the organic layer was washed with water. The combined water layers were twice washed with 150 mL portions of ethyl and then dried. The product was recrystallized from hot trichloromethane/hexane to yield 11.3 g pure product. The product was characterized by GC, GC-MS, $^1$H and $^{13}$C NMR.

b. Preparation of pentamethylbenzyl(N-t-butyl)amino titanium dichloride

To a solution of pentamethylbenzyl(N-t-butyl)amine (2 g, 8.6 mmol) in diethyl ether at −60° C. was added, over 15 minutes, one equivalent of n-butyllithium (5.4 mL, 1.6 M in hexane). Subsequently the temperature of the solution was allowed to warm to room temperature after which it was again cooled to −60° C. Subsequently TiCl$_3$.3THF (3.21 g, 8.7 mmol) was added in one portion. After the temperature of the reaction mixture was raised to room temperature, all solvent was removed under reduced pressure to yield an oil which was used as such.

Polymerization Examples LV–LX

A. Copolymerization of ethylene with propylene was carried out in the following manner:

A stainless steel reactor of 1 liter was charged, under dry N$_2$, with 400 mL of pentamethylheptane (PMH) and 30 μmol triethylaluminum as a scavenger. The reactor was pressurized to 0.9 MPa with purified monomers and conditioned in such a way that the ratio of propylene:ethylene in the gas above the PMH was 1:1. The reactor contents were brought to the desired temperature while being stirred (final volume of about 750 mL).

After conditioning of the reactor, the metal complex (15 μmol) to be used as catalyst component and the cocatalyst (30 μmol BF$_{20}$) were premixed over a period of one minute and fed to the reactor by means of a pump. The mixture was premixed in approximately 25 mL of PMH in a catalyst proportioning vessel, and after-rinsing took place with approximately 75 mL of PMH, always under dry N$_2$ flow.

During polymerization, the monomer concentrations were kept constant as far as possible by supplying the reactor with propylene (125 liters [s.t.p.]/hour) and ethylene (125 liters [s.t.p.]/hour). The reaction was monitored on the basis of the temperature in the reactor and the progress of the monomer infeed.

After 10 minutes of polymerization, the monomer feed was stopped and the solution was drawn off under pressure and collected. The polymer was dried in vacuo for 16 hours at approximately 120° C.

B. Homopolymerization of ethylene and the copolymerization of ethylene with octene were carried out in the following manner:

Six hundred mL of an alkane mixture (pentamethylheptane or special boiling point solvent) were introduced as the reaction medium under dry N$_2$ into a stainless steel reactor having a volume of 1.5 liters. The desired amount of dry octene was then introduced into the reactor (note, this amount is zero for homopolymerization). The reactor was then heated to the desired temperature with stirring, under a desired ethylene pressure.

Into a catalyst proportioning vessel having a volume of 100 mL, 25 mL of the alkane mixture were metered in as a solvent. The desired amount of Al- or B-containing cocatalyst was premixed over a period of one minute with the desired quantity of metal complex.

This mixture was then metered into the reactor, whereupon polymerization was started. The polymerization reaction was carried out isothermally. The ethylene pressure was kept constant at the set pressure. After the desired reaction time of 10 minutes, the ethylene supply was stopped and the reaction mixture was drawn off and quenched with methanol.

The reaction mixture containing methanol was washed with water and HCl, in order to remove residues of catalyst. Then the mixture was neutralized with NaHCO$_3$, after which the organic fraction was admixed with an antioxidant (Irganox 1076®) in order to stabilize the polymer. The polymer was dried in vacuo for 24 hours at 70° C.

In both cases, the following conditions were varied:

metal complex.

type and quantity of scavenger.

type and quantity of cocatalyst.

temperature.

The actual conditions are stated in Table I.

Comonomer incorporation was determined with $^{13}$C-NMR and the molecular weight was determined with gas phase chromatography (GPC).

While the invention has been described in connection with what is presently understood to be practical and preferred embodiments, it is understood that this invention is not to be limited to the disclosed embodiments of cyclopentadiene compounds substituted with a hetero atom-containing group, and methods of making or using such compounds, but on the contrary is intended to cover various modifications and equivalent arrangements included within the spirit and scope of the appended claims.

Thus, it is to be understood that variations in the invention can be made without departing from the novel aspects of this invention as defined in the claims.

TABLE I

| Example | Catalyst complex from Example | Quantity of complex (μmol/0.5 L) | Temperature and pressure | Scavenger | Quantity of scavenger (mmol/0.5 L) | Co-catalyst | Ratio Al/M or B/M | Second monomer | Yield (kg/g-M × 5 min) | Comonomer incorporation (m %) | Molecular weight (MW × 10$^{-3}$) |
|---|---|---|---|---|---|---|---|---|---|---|---|
| LV | XXI | 5 | 150° C. 20 bar | TOA* | 0.2 | BF20* | 2 | octene 18 gr. | 5 | — | — |
| LVI | XVII | 5 | 150° C. 20 bar | TOA | 0.2 | BF20 | 2 | octene 18 gr. | 8 | — | — |
| LVII | XVIII | 10 | 150° C. 20 bar | — | — | MAO* | 1000 | — | 8 | — | — |
| LVIII | XXI | 10 | 120° C. 9 bar | TEA* | 0.02 | BF20 | 2 | propylene ratio 1 | 16 | 45.3 | 23 |
| LIX | XIX | 5 | 150° C. 20 bar | TOA | 0.4 | BF20 | 2 | — | 37 | — | — |
| LX | XXI | 10 | 80° C. 7 bar | — | — | MAO | 2000 | octene 18 gr. | 53 | 4.7 | — |

*Abbreviations:
TOA is trioctylaluminum
TEA is triethylaluminum
BF20 is tetrakis(pentafluorophenyl) borate
MAO is methylaluminoxane from Witco

What we claim is:

1. A metal complex comprising a metal of croup 4, 6 through 10 or a rare earth metal, wherein the metal is in a reduced oxidation state and a polysubstituted cyclopentadiene as a ligand of the metal, wherein at least one substituent of the cyclopentadiene is —RDR'$_n$, in which R is a linking group between the cyclopentadiene and DR'$_n$, D is a hetero atom selected from group 15 or 16 of the Periodic Table of Elements, R' is a hydrocarbon radical, and n is the number of R' groups bound to D.

2. The metal complex according to claim 1, wherein the metal is selected from the group consisting of Ti(III), Zr(III), and Hf(III).

3. The metal complex according to claim 1, wherein the metal complex is cationic.

4. The metal complex according to claim 1, wherein R is (—ER$^3_2$—)$_p$ in which p is an integer from 1 to 4, E is an element from group 14 of the Periodic Table of Elements, and each R$^3$ is separately selected from the group consisting of hydrogen and a hydrocarbon radical.

5. The metal complex according to claim 1, wherein D is selected from the group consisting of N, O, P and S.

6. The metal complex according to claim 5, wherein D is nitrogen.

7. The metal complex according to claim 1, wherein the compound comprising a polysubstituted cyclopentadiene is monoanionic.

8. A metal complex comprising a metal of group 6 through 10 or a rare earth metal and a polysubstituted cyclopentadiene as a ligand of the metal, wherein at least one substituent of the cyclopentadiene is —RDR'$_n$, in which R is a linking group between the cyclopentadiene and DR'$_n$, D is a hetero atom selected from group 15 or 16 of the Periodic Table of Elements, R' is a hydrocarbon radical, and n is the number of R' groups bound to D.

9. The metal complex according to claim 8, wherein R is (—ER$^3_2$—)$_p$ in which p is an integer from 1 to 4, E is an element from group 14 of the Periodic Table of Elements, and each R$^3$ is separately selected from the group consisting of hydrogen and a hydrocarbon radical.

10. The metal complex according to claim 8, wherein D is selected from the group consisting of N, O, P and S.

11. The metal complex according to claim 10, wherein D is nitrogen.

12. The metal complex according to claim 8, wherein the compound comprising a polysubstituted cyclopentadiene is monoanionic.

* * * * *